(12) United States Patent
Laubscher et al.

(10) Patent No.: US 11,642,445 B2
(45) Date of Patent: May 9, 2023

(54) VENTILATION SYSTEM WITH MECHANICAL VENTILATION AND EXTRACORPOREAL BLOOD GAS EXCHANGE

(71) Applicant: HAMILTON MEDICAL AG, Bonaduz (CH)

(72) Inventors: Thomas Laubscher, Rhäzüns (CH); Dominik Novotni, Chur (CH)

(73) Assignee: HAMILTON MEDICAL AG, Bonaduz (CH)

( * ) Notice: Subject to any disclaimer, the term of this patent is extended or adjusted under 35 U.S.C. 154(b) by 682 days.

(21) Appl. No.: 15/316,082

(22) PCT Filed: Jun. 3, 2015

(86) PCT No.: PCT/EP2015/062369
§ 371 (c)(1),
(2) Date: Dec. 2, 2016

(87) PCT Pub. No.: WO2015/185618
PCT Pub. Date: Dec. 10, 2015

(65) Prior Publication Data
US 2017/0095601 A1 Apr. 6, 2017

(30) Foreign Application Priority Data
Jun. 5, 2014 (DE) .................... 10 2014 107 980.9

(51) Int. Cl.
*A61M 1/16* (2006.01)
*A61M 16/00* (2006.01)
*A61M 16/10* (2006.01)

(52) U.S. Cl.
CPC ........ *A61M 1/1601* (2014.02); *A61M 1/1698* (2013.01); *A61M 16/0003* (2014.02);
(Continued)

(58) Field of Classification Search
CPC ........ A61M 1/00; A61M 1/02; A61M 1/0259; A61M 1/10; A61M 1/1006; A61M 1/14;
(Continued)

(56) References Cited

U.S. PATENT DOCUMENTS 5,752,509 A * 5/1998 Lachmann .......... A61M 16/024
128/203.12
5,810,759 A 9/1998 Merz
(Continued)

FOREIGN PATENT DOCUMENTS

WO 2011021978 2/2011

*Primary Examiner* — Colin W Stuart
*Assistant Examiner* — Matthew D Ziegler
(74) *Attorney, Agent, or Firm* — Seed Intellectual Property Law Group LLP

(57) ABSTRACT

A system for supporting the blood gas exchange by means of mechanical ventilation and extracorporeal blood gas exchange comprises a ventilation device for mechanical ventilation of the lungs of a patient, and an ECLS device for the extracorporeal blood gas exchange, wherein the ventilation system is designed to perform mechanical respiratory support by the ventilation device on the one hand and an extracorporeal blood gas exchange by the ECLS device on the other hand in coordinated, automated manner in order to support the gas exchange in the blood circulation of the patient, wherein the ECLS device sets a level of the extracorporeal blood gas exchange, and the ventilation device, on the basis of the level of the extracorporeal blood gas exchange set by the ECLS device, adjusts in automated manner to a level of the mechanical respiratory support.

28 Claims, 12 Drawing Sheets

(52) U.S. Cl.
CPC ..... *A61M 16/022* (2017.08); *A61M 2016/003* (2013.01); *A61M 2016/0027* (2013.01); *A61M 2016/103* (2013.01); *A61M 2016/1025* (2013.01); *A61M 2205/3331* (2013.01); *A61M 2230/005* (2013.01); *A61M 2230/202* (2013.01); *A61M 2230/205* (2013.01); *A61M 2230/432* (2013.01); *A61M 2230/435* (2013.01)

(58) Field of Classification Search
CPC .... A61M 1/16; A61M 1/1601; A61M 1/1603; A61M 1/1698; A61M 1/36; A61M 1/3601; A61M 1/3604; A61M 1/3607; A61M 1/3609; A61M 1/3621; A61M 1/3624; A61M 1/3666; A61M 16/0003; A61M 16/021–024; A61M 16/10–191; A61M 2016/0027; A61M 2016/003; A61M 2016/1025; A61M 2016/103; A61M 2202/0021; A61M 2202/0208; A61M 2202/0225; A61M 2202/04; A61M 2202/0413; A61M 2205/33; A61M 2205/3331; A61M 2205/3303; A61M 2205/3327; A61M 2210/06; A61M 2210/0625; A61M 2210/12; A61M 2230/005; A61M 2230/20; A61M 2230/202; A61M 2230/205; A61M 2230/40; A61M 2230/432; A61M 2230/435

See application file for complete search history.

(56) References Cited

U.S. PATENT DOCUMENTS

| | | | |
|---|---|---|---|
| 6,090,048 A * | 7/2000 | Hertz | A61M 5/16859 600/485 |
| 6,371,114 B1 * | 4/2002 | Schmidt | A61M 16/026 128/204.23 |
| RE38,203 E * | 7/2003 | Kelly | A61M 1/369 128/898 |
| 8,518,326 B2 * | 8/2013 | Brady | A61M 1/3666 422/44 |
| 2004/0184953 A1 * | 9/2004 | Litzie | A61M 1/3629 422/45 |
| 2008/0041381 A1 | 2/2008 | Tham et al. | |
| 2008/0097233 A1 * | 4/2008 | Pedersen | A61B 5/14557 600/531 |
| 2009/0182258 A1 * | 7/2009 | Nogueira Sanches | A61M 1/1698 604/4.01 |
| 2009/0210162 A1 * | 8/2009 | Kristiansen | A61M 1/1698 702/19 |
| 2009/0301492 A1 * | 12/2009 | Wysocki | A61B 5/085 128/204.23 |
| 2015/0034082 A1 * | 2/2015 | Kimm | A61M 16/0051 128/202.16 |

* cited by examiner

VENTILATION SYSTEM WITH MECHANICAL VENTILATION AND EXTRACORPOREAL BLOOD GAS EXCHANGE

CROSS-REFERENCE TO RELATED APPLICATION

The present application claims priority to PCT/EP2015/062369, filed Jun. 3, 2015, which claims priority to Germany 10 2014 107 980.9, filed Jun. 5, 2014, which are incorporated herein by reference in their entirety.

The present invention relates to a ventilation system comprising a device for mechanical ventilation, in particular positive-pressure ventilation, of the lungs of a patient, and an ECLS device for extracorporeal blood gas exchange.

The system is designed to perform mechanical respiratory support by means of the device for mechanical ventilation on the one hand, and extracorporeal blood gas exchange, in particular oxygenation/ventilation, by the ECLS device on the other hand, in coordinated, automated manner in order to support the gas exchange in the blood circulation of the patient. The system is designed specifically for the intensive care of patients, in particular for supporting the pulmonary function and the blood gas exchange, respectively, when, in the course of intensive treatment with mechanical ventilation of a patient, a development towards situations sets in in which mechanical ventilation alone is no longer sufficient for achieving adequate support of the pulmonary function of the patient or in which sufficient support of the pulmonary function would necessitate the setting of ventilation parameters for mechanical ventilation which threaten to cause damage to the lungs and the respiratory tract and/or the cardiovascular system.

According to the invention, the ECLS device sets a level of the extracorporeal blood gas exchange, in particular oxygenation/ventilation, and the device for mechanical ventilation automatically adjusts to a level of the mechanical respiratory support on the basis of the level of the extracorporeal blood gas exchange set by the ECLS device.

The suggested device for mechanical ventilation may be realized as positive-pressure ventilation device, as is common nowadays for mechanical ventilation. In case of positive-pressure ventilation, an external positive pressure is applied to the airway during inspiration, which has the effect that air, possibly with the addition of oxygen and/or other admixtures, is pressed into the lungs. Expiration in most cases takes place passively, by application of ambient pressure to the airway exit, with the pressure in the lungs being released with respect to the ambient pressure. Optionally, there may be some mechanical support during expiration as well. The exchange proper of blood gases, in particular the enrichment of venous blood with O2 and the depletion of CO2 from the venous blood, respectively, as a matter of principle takes place within the lungs in case of mechanical ventilation. The device for mechanical ventilation permits a multiplicity of different ventilation modes, covering a range from forms of assisted spontaneous respiration to forms of completely mechanically controlled ventilation. The device for mechanical ventilation may permit a continuous adaptation of the invasive nature of the ventilation, for example by changing ventilation modes, in accordance with the condition of the patient.

The condition of the patient can be detected by various sensors or measuring procedures which each detect specific parameters, for example—as is usual in mechanical ventilation—the determination of the content of O2 and CO2, respectively, in the inhaled air and the exhaled air, respectively (e.g., as PetCO2 at the end of the expiration phase), or the measurement of the oxygen saturation in the blood by means of pulse oximetry (SpO2), but also beyond this the measurement of the resistance and the compliance of the lungs. It is even possible to detect parameters which during ventilation are commonly detected in sporadic or manual manner only, in particular the content of respiratory gases in the blood by corresponding chemical analysis (PaO2, PaCO2) or by optical measures. All of these measurement procedures may be carried out in automated manner, i.e., without necessitating interventions by physicians or nursing staff.

The device for mechanical ventilation operates in accordance with specific ventilation parameters. These include among others the oxygen concentration in the breathing air (FiO2) supplied to the lungs; the respiratory frequency, i.e., the number of breaths per minute; the tidal volume (also referred to as breathing volume), i.e., the volume of air to be applied into the lungs per breath; the inspiration flow, i.e., the flow of air during the inspiration phase (this may—and as a rule will—indeed vary during a single inspiration phase); the maximum inspiration pressure, i.e., the maximum pressure of the air at the airway entrance during the inspiration phase; the positive end-expiratory pressure (so-called PEEP), i.e., a positive pressure permanently applied to the airway entrance during ventilation in order to counteract the collapsing of parts of the pulmonary alveoli at the end of the expiration phase. The PEEP may be determined in general as pressure at the airway exit at the end of the expiration phase.

The device for mechanical ventilation can perform ventilation on the basis of fixedly preset ventilation parameters, such as FiO2, PEEP or maximum inspiration pressure. Other ventilation parameters may each be matched automatically by the ventilation device so as to achieve a best possible ventilation state. In this regard, the ventilation can be effected such that the device for mechanical ventilation, for a given ventilation mode, automatically sets the relevant flexible ventilation parameters (e.g., by means of respective closed-loop control systems) on the basis of fixedly preset ventilation parameters as well as automatically detected flexible ventilation parameters. The type and number of fixedly preset ventilation parameters and adjustable flexible ventilation parameters are different for different kinds of ventilation modes, such as pressure-controlled ventilation, volume-controlled ventilation, BiPAP ventilation, to name just a few thereof. The lesser the number of fixedly predetermined ventilation parameters, the more flexibly can the ventilation device react to different influences and the lower the number of necessary manual interventions in the ventilation. However, the expenditure necessary for closed-loop control also increases accordingly, and there is in particular the risk that there are combinations of specific ventilation parameters resulting that cause damage to the lungs. For avoiding this, there may be defined specific basic conditions for the flexible ventilation parameters. The respective ventilation parameters then can be varied by the ventilation device within the limits defined for them only.

It is also conceivable that the device for mechanical ventilation can alternate between various ventilation modes, or can select a respective suitable ventilation mode from a plurality of ventilation modes. This can take place in automated manner by evaluation of respectively detected ventilation parameters or parameters characteristic of the ventilation state. As an example, reference is made to the ventilation systems of the applicant known under the designation ASV (Adaptive Support Ventilation), which is included for example in the applicant's device for mechanical ventilation sold under the designation "Si."

In addition to mechanical ventilation, there are various methods for extracorporeal lung support (ECLS) in which the function of the lungs is taken over by a machine in part or completely, in the sense that the exchange of blood gases, i.e., the enrichment of the blood with oxygen (oxygenation) and/or the removal of CO2 from the blood (ventilation), is supported mechanically or takes place even completely mechanically. ECLS as a rule is an intensive-care technology, similar to the heart-lung machine that is frequently employed in heart surgery. While in case of the heart-lung machine, the cardiac functions for maintaining the blood circulation also have to be taken over by the machine completely, ECLS as a rule—though not exclusively—concentrates on the substitution or support of the pulmonary function. Venous-venous ECLS systems as a rule support the pulmonary function by withdrawing blood from the venous system and, after extracorporeal blood gas exchange, returning the same to the venous system. Venous-arterial ECLS systems, in which the blood withdrawn from the venous system, after extracorporeal blood gas exchange, is returned to the arterial system, in addition offer the possibility of mechanical support of the cardiac functions. In connection with the present invention, both venous-venous ECLS systems as well as venous-arterial ECLS systems can be employed. ECLS is used for patients having so severely damaged lungs that the pulmonary alveoli themselves do no longer permit the gas exchange to the extent necessary for securing the respiratory function. ECLS thus is a kind of extracorporeal organ substitution method.

In most ECLS methods, e.g., the so-called extracorporeal membrane oxygenation (ECMO), cannulas are inserted into two large blood vessels (either one or two large veins in case of venous-venous varieties or one large vein and one artery in case of venous-arterial varieties) in order to continuously pump blood through an extracorporeal oxygenator, e.g., a membrane oxygenator in case of ECMO (ECMO=extracorporeal membrane oxygenation) which removes CO2 from the blood and enriches the blood with O2 and then returns the thus processed blood to the blood circulation of the patient. The blood may be returned to the venous system of the patient (so-called veno-venous ECLS), so that the cardiac function is still taken over by the heart. However, there are also forms in which also the heart is bridged and the blood is returned to the arterial system downstream of the heart, in order to support the cardiac function by means of the pump circuit (so-called veno-arterial ECLS). As an alternative to a membrane oxygenator, there may also be used other forms, for example alveoli oxygenators. In some cases, ECLS can be performed in minimally invasive manner, for example by insertion of an integrated gas exchange catheter (IGEC) directly into a large vein. In that event, it is not necessary to take blood from the patient, as the gas exchange takes place in the vein by the capillaries of the catheter supplying O2 and removing CO2, respectively.

ECLS can ensure sufficient oxygenation and ventilation, respectively, for days or weeks and thus gives the lungs time to heal without aggressive mechanical ventilation. Nevertheless, ECLS is considered as a last therapy possibility because of the high technical and personnel expenditure, costs and complication risks (e.g., bleedings).

As a rule, the following parameters can be influenced in ECLS: composition of the gas supplied to the extracorporeal oxygenator (for example the content of O2 and CO2, respectively), the flow of the gas supplied to the extracorporeal oxygenator, the flow of blood through the extracorporeal oxygenator.

The invention is concerned with a ventilation system in which mechanical ventilation and ECLS are intended to be carried out in common in a coordinated manner so as to achieve an as efficient as possible mechanical ventilation with only minor damaging effects for the lungs. The ventilation system is to comprise a device for mechanical ventilation and an ECLS device which each as such can basically be configured in a manner as described hereinbefore.

U.S. Pat. No. 5,810,759 discloses a system featuring automatic control of the ECMO parameters during veno-venous ECMO, with the aim of improving the replacement of CO2 by O2. Respective, preset O2 and CO2 concentrations in the blood can be controlled by control of the blood flow circulating in the ECMO circuit and, proportionally therewith, the oxygenator gas flow supplied to the blood circulating through the ECMO circuit. It is pointed out quite generally that additional external parameters, e.g., settings of a mechanical ventilation device, may be detected and the setting of the parameters of the ECMO system may consider such additional parameters. The document reports of an animal experiment which has shown that the ECMO closed-loop control system is capable to adapt to drastically changed external parameters—in the experiment the drastic reduction of a predetermined respiratory support by mechanical positive-pressure ventilation to a very low level.

The document WO 2011/021978 A1 reveals a ventilation system in which ECLS and positive-pressure ventilation are to be performed in combination and in as automated manner as possible together for supporting the blood gas exchange of a patient. The aim consists in making use of ECLS and positive-pressure ventilation at an optimal level each, in order to avoid damage to the pulmonary system by excessively intensive positive-pressure ventilation. ECLS and positive-pressure ventilation each have a control system of their own for controlling the extracorporeal blood gas exchange and ventilation, respectively. The control systems each have a sensor system of their own associated therewith, delivering respective control parameters for ECLS and positive-pressure ventilation. The control systems for ECLS and positive-pressure ventilation exchange data so that at least one of the control systems outputs a control signal for the process associated therewith on the basis of at least one of the control parameters associated with the other control system. On the one hand, an automatic setting of the support by ECLS is to be effected on the basis of control parameters delivered from positive-pressure ventilation: for a respective level of positive-pressure ventilation, a necessary support level by ECLS is set on the basis of the CO2 content in the breathing gas at the end of the expiration phase. On the other hand, an automatic setting of the support by positive-pressure ventilation is to be effected on the basis of control parameters delivered from the ECLS: for ECLS at the respective level, the necessary support level by positive-pressure ventilation is set on the basis of the O2 content in the blood circulation of the patient. However, it can be seen that in cooperation of the two partial systems, the ventilation system is susceptible of instabilities and complications in operation, as both the partial system ECLS as well as the partial system positive-pressure ventilation will try to counteract a too low level of support—expressed by the control parameter transferred from the respective other partial system. This leads to competition of the two partial systems, with the tendency of a too strong reaction to changes.

Therefore, this system is hardly suitable for a largely automated, coordinated operation of both systems in the scope of a therapy.

According to the invention, there is to be made available a ventilation system which ensures fully automatic ventilation in more reliable manner, in particular in situations in which mechanical ventilation and ECLS are applied simultaneously, as mechanical ventilation alone involves the risk of an insufficient blood gas exchange and/or the risk of irreparable damages to lungs, respiratory tract or cardiovascular system. This ventilation system is to be designed in particular for use in intensive medical treatment of patients with lacking or at least insufficient respiratory function, which necessitates mechanical ventilation.

With the inventive combination of a conventionally operating device for mechanical ventilation, in particular positive-pressure ventilation, with a device for extracorporeal lung support ECLS (in particular a device for extracorporeal membrane oxygenation ECMO), the ECLS device determines, by evaluation of a parameter—this may be a parameter determined in the ECLS device, e.g., the content of O2 flowing through the extracorporeal circuit or in the venous blood downstream of the extracorporeal oxygenation, but also a parameter delivered from mechanical ventilation—, whether the intensity of the treatment by ECLS as compared to the intensity of mechanical ventilation is to be changed. Transferred to the mechanical ventilation is, as predetermined parameter, at least one parameter indicating the relative proportion of the intensity of the ECLS treatment. The mechanical ventilation then adjusts to a particular situation, or at least tries to adjust such that a particular state is achieved. Thus, as regards the course of the therapy, there is always ECLS dominating over mechanical ventilation. ECLS is preset with a predetermined level of support. The mechanical ventilation adjusts, taking the support level of the ECLS as preset factor.

The further course of the therapy is determined in that the ECLS device examines to what extent the set support level is to be maintained or is to be altered (as a rule reduced). If the level of the ECLS support is to be reduced, a parameter distinguishing the new level of the ECLS support will be transferred to the device for mechanical ventilation as new specification for the automatic setting of the mechanical ventilation. This can be effected, for example, such that the ECLS device sets a target value for the level of the extracorporeal blood gas exchange. The ECLS device comprises (closed-loop) control mechanisms operating with the aim that the ECLS device, in consideration of currently detected blood gas values, attempts to approach the preset target value and then maintains a target value once reached. The mechanical ventilation each time adapts to a respective state of the ECLS device prevailing in the course of this approach to the target value, and thus indirectly also follows a development towards a ventilation state matched to the preset target value.

A possible control strategy may consist in that ECLS is set initially with an as high as possible support level, in particular a support level at which the necessary support of the pulmonary function can be afforded completely by ECLS and without support by mechanical ventilation (i.e., with an ECLS support level of 100%). Thereafter, it is regularly examined (as a rule by the ECLS control unit) to what extent the ECLS support level can be reduced and the support level by machine ventilation can be increased accordingly.

The device for mechanical ventilation tries, for a respective given setting of the ECLS device, as characterized by such parameters as flow of blood in the ECLS circuit, total gas flow of O2 and other gases, respectively, to the oxygenator, composition of the oxygenator gas, to set the parameters for mechanical ventilation such that given target values for the gas exchange are achieved. In this sense, the suggestion according to the invention means that ECLS is "dominant" as compared to mechanical ventilation. The device for mechanical ventilation deems a state set by ECLS as given state and tries to adjust a suitable state of the mechanical ventilation for this given state. In this regard, the mechanical ventilation is tied to specific requirements for the—depending on the particular ventilation mode—fixedly preset ventilation parameters, but indeed also to specific basic conditions for adjustable ventilation parameters, such as maximum PEEP, maximum airway pressure or maximum minute volume of the ventilation gas supplied. The minute volume is a result of the product of the respiratory frequency and the respective tidal volume applied in one breath.

The level of the extracorporeal blood gas exchange by the ECLS device may be preselected in automated or manual manner. Of particular interest is the possibility of automated presetting of the level of the extracorporeal blood gas exchange by the ECLS device in the scope of an ECLS adjustment strategy, as it will be explained in more detail in the following in the form of an example.

The device for mechanical ventilation, for example, may be designed such that, for a respective setting made as regards the level of the extracorporeal blood gas exchange by the ECLS device, the respiratory support by mechanical ventilation is (open-loop/closed/loop) controlled automatically. For example, the device for mechanical ventilation may be designed to select, in automated manner and in the scope of predetermined ventilation parameters, a ventilation state to the set by the device for mechanical ventilation, and to control the device for mechanical ventilation such that the latter assumes the selected ventilation state or at least tries to assume the selected ventilation state. This may be provided in particular in the form of mechanical ventilation using a closed-loop control system. Ventilation devices offering sufficient flexibility with respect to the respective ventilation mode to be selected and, moreover, capable of automatically selecting a specific ventilation mode that appears to be suitable, for example are ventilation devices encompassing the ventilation mode known under the designation "ASV" (=Adaptive Support Ventilation). ASV offers ventilation with a closed-loop control system and dynamic computation of optimum ventilation modes and, upon selection of a ventilation mode, of the still necessary automatic settings of the free parameters of the respective ventilation mode selected, so that sufficient respiratory support can be achieved with as little effects on the patient as possible. In doing so, lung-protecting treatment strategies operating with as low pressures as possible are preferred. The ventilation parameters set for the device for mechanical ventilation can be derived from the level of the extracorporeal blood gas exchange set by the ECLS device. For example, the maximum end-expiratory pressure PEEPmax in mechanical ventilation or the maximum airway pressure (PEEP+Pinsp)max in mechanical ventilation or the maximum minute volume in mechanical ventilation may be dependent on the respective level set of the extracorporeal blood gas exchange.

For example, it is possible to assign to the level of the extracorporeal blood gas exchange set by the ECLS device a degree of the extracorporeal support in oxygenation, i.e., when enriching the blood with oxygen. The degree of extracorporeal support in oxygenation in particular may be a relative value relating to the proportion of the extracorporeal oxygenation in the enrichment of the blood with oxygen in total, i.e., the enrichment of the blood with oxygen effected in total by extracorporeal oxygenation and mechanical ventilation. This proportion will also be referred to as % ECLS_O2 in the following. The respective degree of extracorporeal support in oxygenation % ECLS_O2 may then determine a maximum positive end-expiratory pressure PEEPmax for mechanical ventilation. The maximum positive end-expiratory pressure (PEEPmax) may then increase with decreasing degree of the extracorporeal support in oxygenation % ECLS_O2. It is ensured in this manner that the maximum positive end-expiratory pressure—which in numerous ventilation modes of mechanical ventilation constitutes a basic condition for the intensity of ventilation—increases more and more the lower the degree of extracorporeal support in oxygenation % ECLS_O2 becomes. This entails accordingly an increase in the level of the support in enriching blood with O2 by mechanical ventilation as compared to the level of support by extracorporeal oxygenation. The relevance of the mechanical ventilation increases more and more as the degree of extracorporeal support in oxygenation decreases. The function of the lungs as a (natural) organ for enriching the blood with O2 accordingly gains increasing significance the longer the combination of mechanical ventilation and ECLS operates in satisfactory manner. This is in line with the fact that the positive end-expiratory pressure PEEP set in mechanical ventilation may assume higher and higher maximum values the longer the combination of mechanical ventilation and ECLS support takes place in satisfactory manner. A higher positive end-expiratory pressure, on the one hand, results in more efficient mechanical ventilation as a collapse of pulmonary alveoli during expiration can be suppressed better, but on the other hand means also a higher load for the pulmonary tissue.

A change of the level of the extracorporeal blood gas exchange is the direct result of the forced alteration of the proportion of the mechanical ventilation as compared to the proportion of the extracorporeal blood gas exchange.

An alteration of the level of extracorporeal blood gas exchange can also be obtained directly in that the degree of extracorporeal support in oxygenation % ECLS_O2 determines a maximum value for the flow of the blood taken from the patient by the ECLS device. It may be provided in this regard that the maximum value for the flow of the blood taken from the patient by the ECLS device increases as the degree of the extracorporeal support in oxygenation % ECLS_O2 increases. This measure may be used instead of the aforementioned relationship between maximum positive end-expiratory pressure and degree of the extracorporeal support in oxygenation. However, it is particularly efficient to employ this measure in addition.

In addition or as an alternative it is also possible to assign a degree of the extracorporeal support in ventilation, i.e., in depleting CO2 from the blood, to the level of extracorporeal blood gas exchange. Also the degree of extracorporeal support in ventilation may be in particular a relative value relating to the proportion of the extracorporeal ventilation in depleting CO2 from the blood in total, i.e., the depletion of CO2 from the blood effected in total by extracorporeal ventilation and mechanical ventilation (artificial respiration). This proportion will also be referred to as % ECLS_CO2 in the following.

The degree of extracorporeal support in ventilation % ECLS_CO2 may be independent of the degree of extracorporeal support in oxygenation % ECLS_O2.

The degree of extracorporeal support in ventilation % ECLS_CO2 may determine a maximum minute volume (the minute volume is defined as tidal volume multiplied by the respiratory frequency) for mechanical ventilation. In particular, the maximum minute volume may increase with a decreasing degree of the extracorporeal support in ventilation % ECLS_CO2. In addition or as an alternative, the degree of extracorporeal support in ventilation % ECLS_CO2 may determine a maximum airway pressure (the airway pressure is defined as the sum of the positive end-expiratory pressure PEEP and the pressure prevailing during inspiration and expiration, respectively, with the highest airway pressure usually being reached at the end of inspiration) for mechanical ventilation. In particular, the maximum airway pressure may increase with a decreasing degree of the extracorporeal support in ventilation % ECLS_CO2. It turns out particularly favorable when the maximum airway pressure is not only derived from the degree of extracorporeal support in ventilation, but also from the degree of extracorporeal support in oxygenation, in particular from the respective higher one of the two degrees. It is possible, for example, for deriving the maximum airway pressure in mechanical ventilation, to utilize a relationship to the maximum airway pressure that is increasing as the degree of the maximum value of extracorporeal support in oxygenation (% ECLS_O2) and extracorporeal support in ventilation (% ECLS_CO2) is decreasing.

The effect achieved in this manner is that the maximum airway pressure and/or the maximum minute volume—these parameters, too, constitute basic conditions for the intensity of ventilation in many ventilation modes of mechanical ventilation—continues to increase the more the lower the degree of the extracorporeal support in ventilation % ECLS_CO2 becomes, possibly with additional consideration of the degree of extracorporeal support in oxygenation. Thus, the level of support in depleting CO2 by mechanical ventilation increases accordingly as compared to the level of support by extracorporeal ventilation. The mechanical ventilation gains increasing significance the lower the degree of extracorporeal support in ventilation becomes. Thus, here too, the function of the lungs as a (natural) organ for depleting CO2 from the blood gains increasing significance the lower the degree of extracorporeal support in ventilation becomes. This is in line with the fact that mechanical ventilation at higher maximum limit values for the airway pressure and/or the minute volume may have the tendency to effect more efficient expiration, however once again with an in total higher load acting on the pulmonary tissue.

In this event, too, it is also possible to directly achieve an alteration of the level of extracorporeal blood gas exchange when the degree of extracorporeal support in ventilation % ECLS_CO2 determines a maximum value of the flow of oxygenation gas that the ECLS device supplies to the blood taken from the blood circulation of the patient. In particular, the maximum value of the flow of oxygenation gas that the ECLS device supplies to the blood taken from the blood circulation of the patient may increase with an increasing degree of the extracorporeal support in ventilation % ECLS_CO2. As an alternative or in addition thereto, it would also be possible to change the composition of the oxygenation gas. This measure, too, may be employed instead of the correlations indicated hereinbefore between maximum airway pressure and/or maximum minute volume on the one hand and the degree of extracorporeal support in ventilation on the other hand. However, it is particularly efficient to make use of this measure in addition.

A ventilation system that reliably operates in automated manner to a large extent—if desired, even completely—will provide as a rule that the ECLS device—with a set value for the level of the extracorporeal blood gas exchange—examines upon expiration of a predetermined period of time whether, with regard to the set value for the level of the extracorporeal blood gas exchange, a predetermined target state for the blood gas exchange is reached by the device for mechanical ventilation and the ECLS device together.

The predetermined target state for the blood gas exchange may be expressed, for example, by a parameter that is characteristic of the content of O2 in the blood circulation. To this end, there may be used in principle all common methods or parameters that are suitable for expressing a content of O2 in the blood. In particular, one of the following parameters will be readily used: SpO2 (saturation value of O2 in venous blood determined by pulse oximetry; for this purpose, there are available fingertip probes that are particularly easy to use), SaO2 (saturation value of oxygen in the blood, determined by chemical analysis or by optical methods) or PaO2 (partial pressure of O2 in the blood). These values can be measured in the device for mechanical ventilation (e.g., by pulse oximetry) or in the ECLS device (this is useful in blood gas analyses as a flow of blood is branched off from the vascular system of the patient anyway). The position of the measurement probes may basically be situated downstream or upstream of the location where the blood gas exchange takes place.

In corresponding manner, it is possible in addition or as an alternative to characterize the predetermined target state for the blood gas exchange by a parameter that defines the content of CO2 in the blood circulation. Here too, it is possible to make use of all known methods or parameters suitable for expressing a content or concentration of CO2 in the blood, e.g., PaCO2 (partial pressure of CO2 in the blood), PetCO2 (content of CO2 in the breathing air, measured at the end of the expiration phase). Also the measurement of the blood gas exchange as regards CO2 can be effected both in the device for mechanical ventilation (e.g., PetCO2) or in the ECLS device (e.g., PaCO2). The statements made hereinbefore with regard to the content of O2 apply analogously.

A particularly expedient development provides that the ECLS device, upon reaching the predetermined target state, reduces the level of the extracorporeal blood gas exchange. This means that the ECLS device has an inherent tendency to successively reduce the level of the extracorporeal blood gas exchange—in the favor of the blood gas exchange effected by mechanical ventilation—from an initial level in ongoing manner. The result hereof is that the ventilation system includes an inherent weaning effect from the extracorporeal blood gas exchange: the extracorporeal blood gas exchange tends to be decreased further and further as long as the mechanical ventilation—for the given level of the extracorporeal blood gas exchange—can adjust to a state at which a predetermined target state is reached. As was already explained, the predetermined target state in particular is a desired state as regards the achieved enrichment of the blood with oxygen and/or the achieved depletion of CO2 from the blood.

The desired weaning functionality can be achieved in particularly elegant manner in that the ECLS device, upon determination that the target state can be reached, in particular that the set value for the concentration of O2 in the blood circulation can be reached, reduces the degree of extracorporeal support in oxygenation % ECLS_O2 by a first predetermined amount. As explained hereinbefore, this has the effect that the proportion of mechanical ventilation in the support of blood gas exchange, in particular in the enrichment of the blood with oxygen, is further increased at the expense of the proportion of the extracorporeal support in oxygenation. The total level of support in blood gas exchange, in particular in oxygenation, by the ECLS device and the device for mechanical ventilation together does not necessarily need to change. Rather, it will remain constant in many cases, in accordance with the fact that the total necessary support level has not changed. However, what does shift in increasing manner in the course of time is the proportion of the mechanical ventilation in the support administered in total. This is due to the fact, for example, that the mechanical ventilation in total may take place in the scope of increasingly lenient boundary conditions, e.g., for the positive end-expiratory pressure PEEP, as the maximum end-expiratory pressure increases with decreasing degree of support by extracorporeal membrane oxygenation % ECLS_O2. A contribution also resides in the fact that the maximum flow of the blood taken from the patient becomes increasingly smaller with a decreasing degree of support by extracorporeal membrane oxygenation % ECLS_O2.

Accordingly, it is possible as an alternative or in addition that the ECLS device, upon determination that the target state can be reached, in particular that the preset value for the concentration of CO2 in the blood circulation can be reached, to reduce the degree of the extracorporeal support in ventilation % ECLS_CO2 by a second predetermined amount. The statements made hereinbefore in relation to the degree of extracorporeal support in oxygenation % ECLS_O2 apply in this case analogously: the proportion of mechanical ventilation in the support of the blood gas exchange, in particular in the depletion of carbon dioxide from the blood, is increased more and more, at the expense of the proportion of the extracorporeal support in ventilation. The overall level of support in the blood gas exchange, in particular in ventilation by the ECLS device and the device for mechanical ventilation together, need not necessarily change. Rather, it will remain constant in many cases, in accordance with the fact that the total necessary support level has not changed. However, what does shift in increasing manner in the course of time is the proportion of the mechanical ventilation in the support administered in total. The mechanical ventilation in total may take place in the scope of increasingly lenient boundary conditions, e.g., for the maximum airway pressure and/or the maximum tidal volume, as the maximum airway pressure and/or the maximum tidal volume increases more and more with a decreasing degree of support by extracorporeal ventilation % ECLS_CO2. A contribution also resides in the fact that the maximum flow of the oxidation gas supplied to the blood taken from the patient becomes increasingly smaller with decreasing degree of support by extracorporeal ventilation % ECLS_CO2.

In case the predetermined target value is even exceeded, provisions can be made that the ECLS device reduces the level of extracorporeal oxygenation. In particular, it may be provided that the ECLS device, upon exceeding the predetermined value of the concentration of O2 in the blood circulation, reduces the flow of the blood taken from the blood circulation of the patient by the ECLS device and/or reduces the degree of extracorporeal support in oxygenation. In particular, provisions can be made that the ECLS device, when the predetermined value for the concentration of CO2 in the blood circulation is exceeded, reduces the flow of oxygenation gas supplied to the blood taken from the patient's blood circulation by the ECLS device and/or reduces the degree of extracorporeal support in ventilation % ECLS_CO2. The reduction of the degree of extracorporeal support in oxygenation or of the degree of extracorporeal support in ventilation, respectively, is made in particular by a larger amount than in the case that the respective predetermined target value is indeed reached, but not exceeded.

If the predetermined target value is not reached, stopping or a certain reversal of the process may be provided for. This can be achieved in that the ECLS device increases the level of extracorporeal oxygenation and the level of extracorporeal ventilation, respectively, by a predetermined amount each. This scenario also permits hazardous situations to be taken account of, by providing an increase in the level of extracorporeal oxygenation and the level of extracorporeal ventilation, respectively, by a clearly higher amount when the respective target value is clearly missed and/or there is no tendency whatsoever ascertainable for an approximation to the respective target value.

A ventilation system that approaches a state with the highest possible proportion in mechanical ventilation in largely autonomous manner, with the proportion of extracorporeal blood gas exchange being as high as necessary, can be realized in particular in that the ECLS device examines in recurrent intervals of time whether a predetermined target value for the blood gas exchange can be reached at the respective set value for the level of extracorporeal blood gas exchange by the device for mechanical ventilation and the ECLS device together. This examination can be made in the manner outlined hereinbefore and may have the consequences indicated hereinbefore.

The time interval for the examination by the ECLS device will have to be selected according to the rule "as small as possible, as large as necessary." In this regard, there may be utilized the fact that the device for mechanical ventilation is capable of adjusting to changed circumstances within very brief timescales. In contrast thereto, extracorporeal blood gas exchange demands a clearly stronger intervention, which also means that strong repercussions on the patient have to be expected. It is therefore suggested to match the parameters for the extracorporeal blood gas exchange as slowly and as continuously is possible. This can be taken account of by selecting the time intervals for the examination by the ECLS device to be clearly greater than the time constant of the device for mechanical ventilation, i.e., the time the device for mechanical ventilation needs on the average for adjusting to a change in the preset parameters. The suggested combination of the cooperation of ECMO, as a partial system defining the course of the therapy to a large extent, with mechanical ventilation, as a partial system adjusting thereto, favors this approach as it inherently permits to select the time interval of the examination by the ECLS device to be rather large, in any case much larger than the time constant of mechanical ventilation. For example, the device for mechanical ventilation may be designed such that it provides a new setting with each breath, i.e., performs control on a breath-by-breath basis.

Basically, the procedure can be such that the ECLS device starts from a preset starting value for the level of extracorporeal oxygenation/ventilation and then, in cooperation with the device for mechanical ventilation, largely autonomously, i.e., without obligatory manual interventions, reaches a state in which both partial systems operate in largely optimum manner. This state may also change in the course of the therapy, for example when there are changes in the condition of the patient necessitating an adaptation of mechanical ventilation and/or of extracorporeal blood gas exchange. It is particularly expedient when the starting value corresponds to a maximum level for the level of extracorporeal oxygenation/ventilation. One then starts from a state in which the blood gas exchange is effected virtually completely by the ECLS device and without the device for mechanical ventilation. Starting from this state, the ventilation system adjusts the level of extracorporeal blood gas exchange and mechanical ventilation step by step, with the proportion of extracorporeal blood gas exchange being reduced more and more and the proportion of mechanical ventilation being accordingly increased step-by-step.

It is expedient when the ventilation system uses the starting value as reference value for the reduction(s) and increase(s), respectively, of the level of extracorporeal oxygenation/ventilation taking place in the further course.

In addition to this, the present invention also relates to a method of operating, in coordinated manner, a device for mechanical ventilation of the lungs of a patient and an ECLS device for extracorporeal blood gas exchange of the patient's blood, in which mechanical respiratory support by the device for mechanical ventilation on the one hand and extracorporeal blood gas exchange by the ECLS device, on the other hand, are performed in coordinated, automated manner so as to support the gas exchange in the patient's blood circulation. In this method, the ECLS device sets a level of extracorporeal blood gas exchange, and the device for mechanical ventilation, on the basis of the level of extracorporeal blood gas exchange set by the ECLS device, adjusts in automated manner to a level of the mechanical respiratory support. Such a method can be developed further in preferred developments, as described hereinbefore.

BRIEF DESCRIPTION OF THE SEVERAL VIEWS OF THE DRAWINGS

The invention will be explained in more detail in the following on the basis of embodiments illustrated in the drawings, wherein.

DETAILED DESCRIPTION

Figure 1:
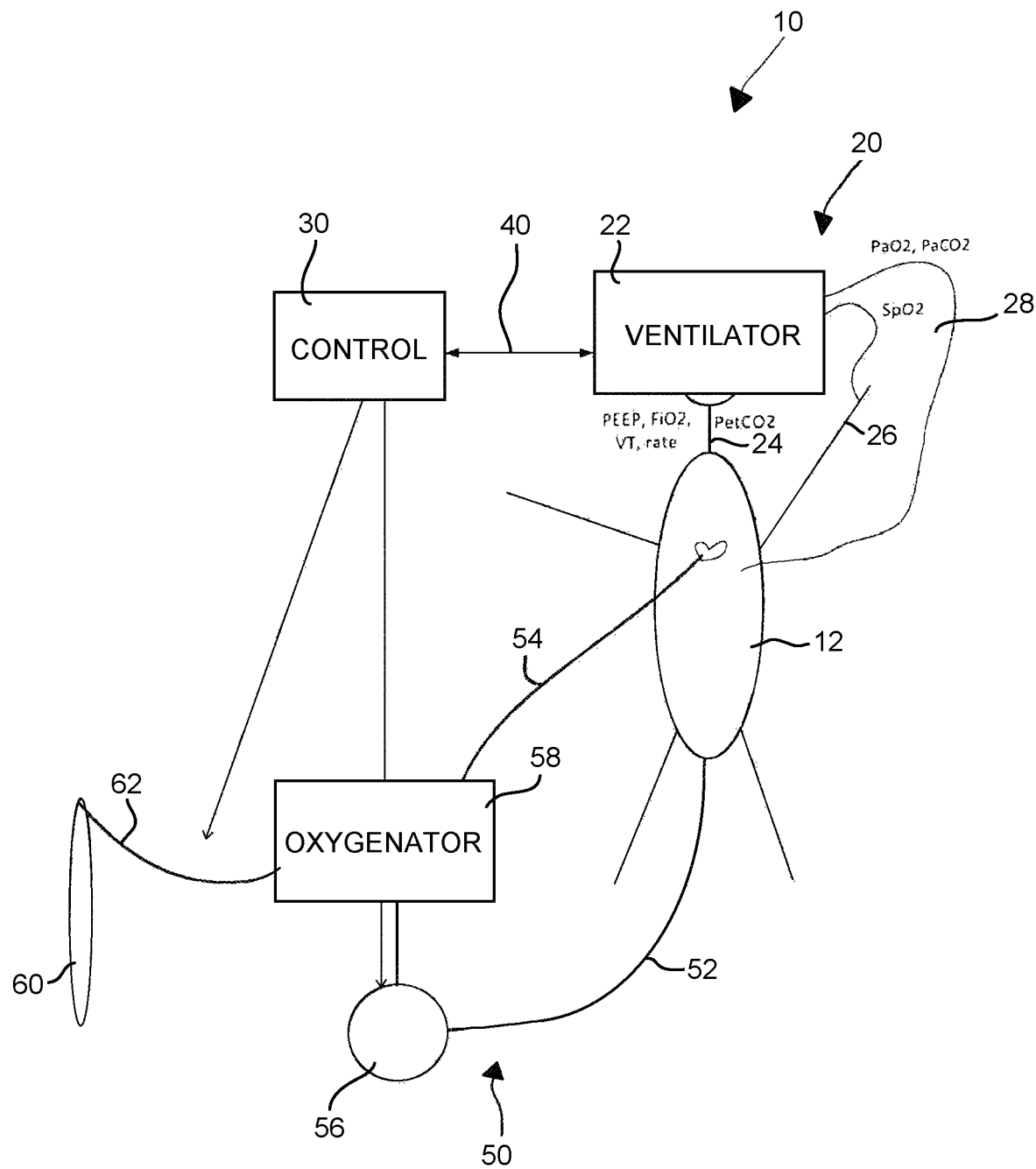
FIG. 1 shows a schematic, highly simplified view of a ventilation system according to the invention, comprising a device for mechanical ventilation designed as positive-pressure ventilation device, as well as an ECLS device.

FIG. 1 shows in a schematic and highly simplified view a ventilation system 10 according to the invention, comprising a device 20 for mechanical ventilation designed as positive-pressure ventilation device, and an ECLS device 50. The ventilation device 20 comprises a ventilator 22 shown merely schematically in FIG. 1. The ventilator 22 is connected, via a conduit system 24 not shown in more detail, to the airway of a patient (illustrated schematically in FIG. 1 and designated 12). Via the conduit system 22, the ventilator 22 supplies pressurized air to the airway of the patient 12 during inspiration phases and discharges air from the patient's airway during expiration phases. During ventilation, the conduit system 22 permanently has a positive end-expiratory pressure PEEP applied thereto. Added to this pressure, during the inspiration phases, is an inspiration pressure Pinsp that is also applied by the ventilator (and which as a rule changes during the inspiration cycle). During the expiration phases, the ventilator as a rule applies only the positive end-expiratory pressure PEEP with respect to which the lung tissue relaxes.

The ventilation device 20 furthermore is equipped with a sensor system for detecting parameters essential for ventilation. For example, the following parameters partly illustrated in FIG. 1 are detected in the conduit system 24: inspiration pressure Pinsp, expiration pressure Pexp, positive end-expiratory pressure PEEP, tidal volume VT (i.e., breathing gas volume applied into the lungs during an inspiration cycle), flow quantity of the breathing gas applied, positive pressure of CO2 in the breathing gas (in particular during expiration). The ventilation device 20 moreover comprises sensor means for determining the oxygen saturation in the patient's blood, illustrated in FIG. 1 at numeral 26. This may be provided in the form of a pulse oximetry sensor means (e.g., with fingertip sensor) for subcutaneous determination of the arterial oxygen saturation SpO2. In the embodiment illustrated in FIG. 1, the ventilation device 20 comprises furthermore sensor means for analyzing blood gases, in particular for determining the arterial concentration of oxygen in the blood PaO2 and for determining the arterial concentration of carbon dioxide in the blood PaCO2 in recurrent intervals, as shown schematically in FIG. 1 at numeral 28. Instead of the concentrations PaO2 and PaCO2 of oxygen and carbon dioxide, respectively, there may also be determined the corresponding saturations in hemoglobin SaO2 and SaCO2.

The ventilation device 20 has a controller associated therewith, which is designed for controlling all procedures of the ventilation device in largely automated manner. This controller may be integrated in the ventilator 22, but may also be designed in part or even completely as external controller. The controller for the ventilation device 20 comprises the usual interfaces for communication with operating personnel, in particular for displaying the ventilation state of the patient and for inputting control commands. The controller basically is designed such that the ventilation device 20 selects suitable ventilation modes largely autonomously and without manual interventions, respectively, and, in the scope of a preselected ventilation mode, sets the ventilation parameters to optimum values each and, in the sense of closed-loop control systems, also autonomously monitors the ventilation parameters and possibly readjusts the same, so that a desired ventilation state can be maintained, if possible.

Ventilation devices of this kind, for example, are devices encompassing largely automated ventilation modes, for example the ventilation mode known under the designation "Adaptive Support Ventilation" which is realized in ventilation devices of the applicant.

For additional support of the blood gas exchange, the ventilation system 10 in FIG. 1 is provided with an ECLS device (ECLS=extracorporeal lung support), generally indicated at 50. In contrast to the ventilation device 20 that is connected to the patient's airway and applies breathing gas to the lungs via the airway, the ECLS device 50 serves to support the exchange of blood gases directly, i.e., to substitute the function of the lungs partially or even completely. The ECLS device 50 therefore is not coupled to the lungs, but directly to the blood circulation of the patient. The ECLS device 50 comprises a first conduit 52 via which blood is withdrawn from the venous system of the patient and is fed to an extracorporeal blood circulation of the ECLS device. The extracorporeal blood circulation is driven by an ECLS pump 56 which supplies the blood taken from the venous system to an oxygenator 58 and then returns the same via a further conduit 54 to the patient's blood circulation. In case of veno-venous extracorporeal blood gas exchange support, the additional conduit 54 returns the blood enriched with oxygen and depleted from CO2 to the patient's venous system. There are also conceivable forms of veno-arterial extracorporeal blood gas exchange support, in which the additional conduit 54 conveys the blood enriched with oxygen and depleted from CO2 back to the patient's arterial system downstream of the heart, so as to support also the patient's cardiac function in addition to the pulmonary function. In that case, the ECLS device 50 in terms of its function is very similar to a heart-lung machine.

In the oxygenator 58 the venous blood is depleted from CO2 and enriched with O2. To this end, an oxygenation gas 62 is supplied to the oxygenator 58, which in the oxygenator 58 interacts with the venous blood so as to take up CO2 from the hemoglobin, and to apply O2 to the hemoglobin released thereby. The oxygenator 58 thus substantially takes over the function of the alveoli in the lungs. Such oxygenators 58 are known for example in heart-lung machines. When provided in the form of a membrane oxygenator, a semi-permeable membrane is used for exchange of the blood gases O2 and CO2, with the support in blood gas exchange afforded by the ECLS device being known under the designation ECMO (extracorporeal membrane oxygenation). There are also other oxygenator constructions known and basically usable as well. The oxygenation gas 62 has its origin in a conditioning unit 60 and basically is a gas mixture enriched with O2, sometimes also pure O2. The extent of the desired oxygenation and ventilation, respectively, can be set by the partial pressures of O2 and CO2, respectively, in the oxygenation gas 62. To this end, the oxygenation gas may be suitably conditioned, if desired this can be effected in accordance with the composition of blood gases in the venous system from which the extracorporeal blood gas flow is taken, or in the arterial system.

The fundamental parameters for controlling the level of blood gas exchange support by the ECLS device 50 are the flow of the blood taken from the body and pumped through the extracorporeal circuit, as well as the flow of the oxygenation gas supplied to the oxygenator. The flow of the blood taken from the body and pumped through the extracorporeal circuit can be detected quite easily by the pump flow generated by pump 58, and can be adjusted. It is also easily possible to detect and adjust the flow of the oxygenation gas by means of suitable flow sensors or flow controls.

In addition, there is also the possibility to take suitable influence on the composition of the oxygenation gas, as described hereinbefore. For example, it is indeed possible to add a certain amount of CO2 to the oxygenation gas in order to suppress negative physiologic effects of an excessive depletion of CO2.

For controlling the ECLS parameters, there is provided an ECLS control unit indicated in FIG. 1 as separate control device and shown at numeral 30. The ECLS control unit 30 detects the data mentioned as regards the flow of the blood taken from the body and pumped through the extracorporeal circuit as well as the flow of the oxygenation gas supplied to the oxygenator, and also as regards the composition of the oxygenation gas. In response to these data, the ECLS control unit issues suitable control commands to the ECLS pump 56, the oxygenator 58 and the oxygenation gas generator 60 as well as to actuators associated with the same, in order to set the respectively desired flows and compositions, as a rule via corresponding closed-loop control systems (e.g., PI control systems). This is illustrated in FIG. 1 by way of respective arrows.

The control unit associated with the ventilation device as well as the control unit associated with the ECLS device operate generally in mutually independent manner. However, they exchange data via a connection illustrated at numeral 40 in FIG. 1 so as to render possible a coordinated mode of operation of the ventilation device 20 on the one hand and the ECLS device 50 on the other hand. This will be described in more detail in the following.

However, it should already be pointed out here that a physical separation of the control unit 30 associated with the ECLS device 50 and the control unit associated with the ventilation device 20 is not absolutely necessary. It is indeed conceivable to physically combine both control units in one unit or module. Such a unit or module may be provided as an independent unit in addition to the ventilation device 20 and the ECLS device 50, but may also be fully integrated in one of these devices, e.g., in the ventilator 22 shown in FIG. 1.

Figure 2:
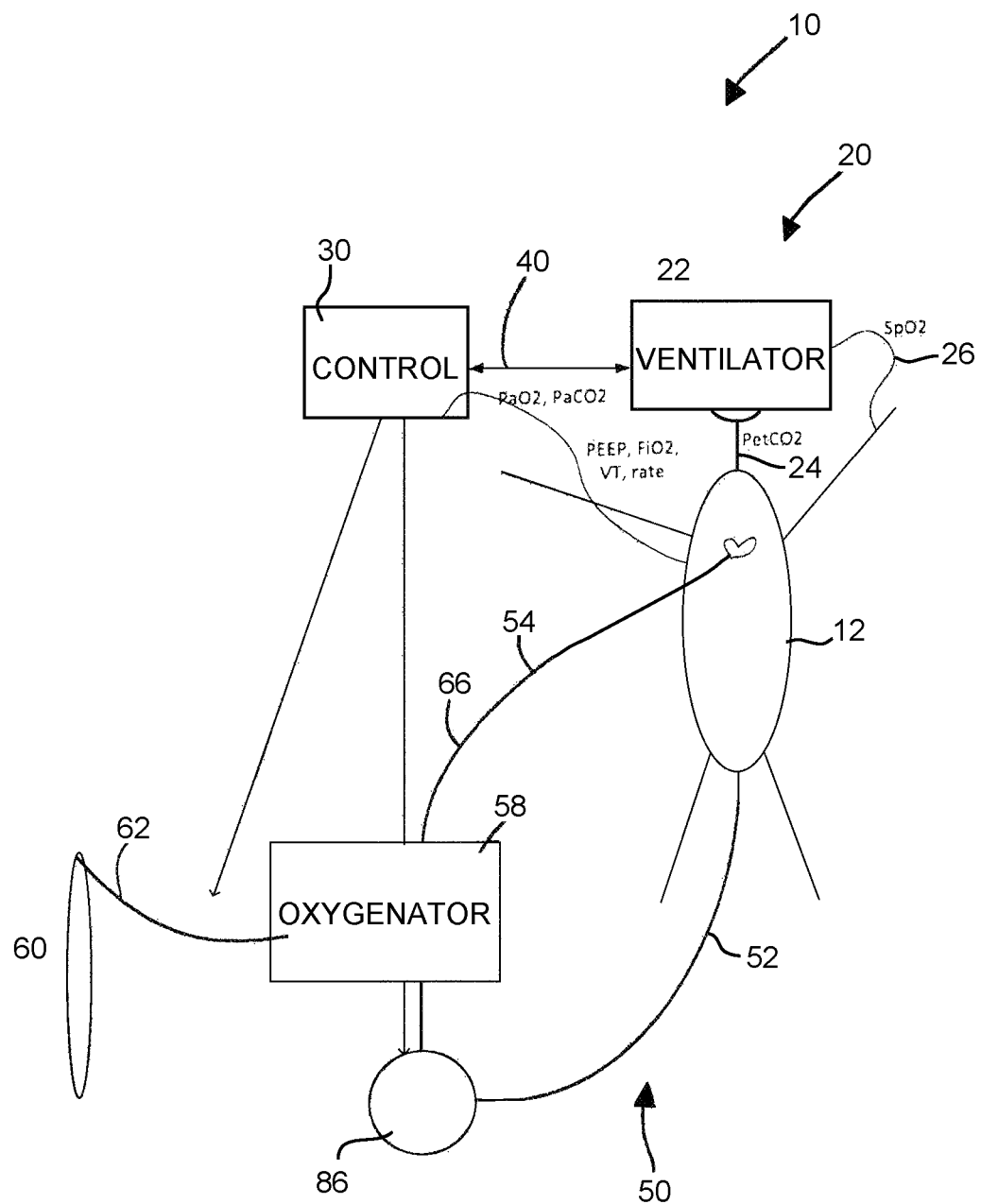
FIG. 2 shows a schematic, highly simplified view according to FIG. 1, illustrating a further ventilation system according to the invention, comprising a device for mechanical ventilation designed as positive-pressure ventilation device, as well as an ECLS device.

FIG. 2 shows, in a schematic and highly simplified view according to FIG. 1, another ventilation system 10 according to the invention, comprising a ventilation device 20 and an ECLS device 50. The reference numerals used in FIG. 2 are in correspondence with those of FIG. 1, in so far as the same or corresponding components are present. In this regard, reference is made to the description of these components in relation to FIG. 1, which applies analogously. The ventilation system according to FIG. 2 differs from that according to FIG. 1 merely in that the sensor system for determining the concentration or saturation of O2 and CO2 (in the form PaO2 and PaCO2, respectively, or in the form SaO2 and SaCO2, respectively) in the patient's blood circulation is no longer associated with the ventilation device 20, but is associated with the ECLS device 50. As indicated by numeral 66, the determination of PaO2/PaCO2 (or SaO2/SaCO2) takes place in the extracorporeal blood circulation. This is expedient in particular in the light of the fact that such a sensor system can easily be accommodated in the extracorporeal blood circulation and as such information as a rule is necessary anyway for operation of the ECLS device 50. Via the interface 40, the data detected in the ECLS blood circulation then are also available for the ventilation device 20.

Figure 3:
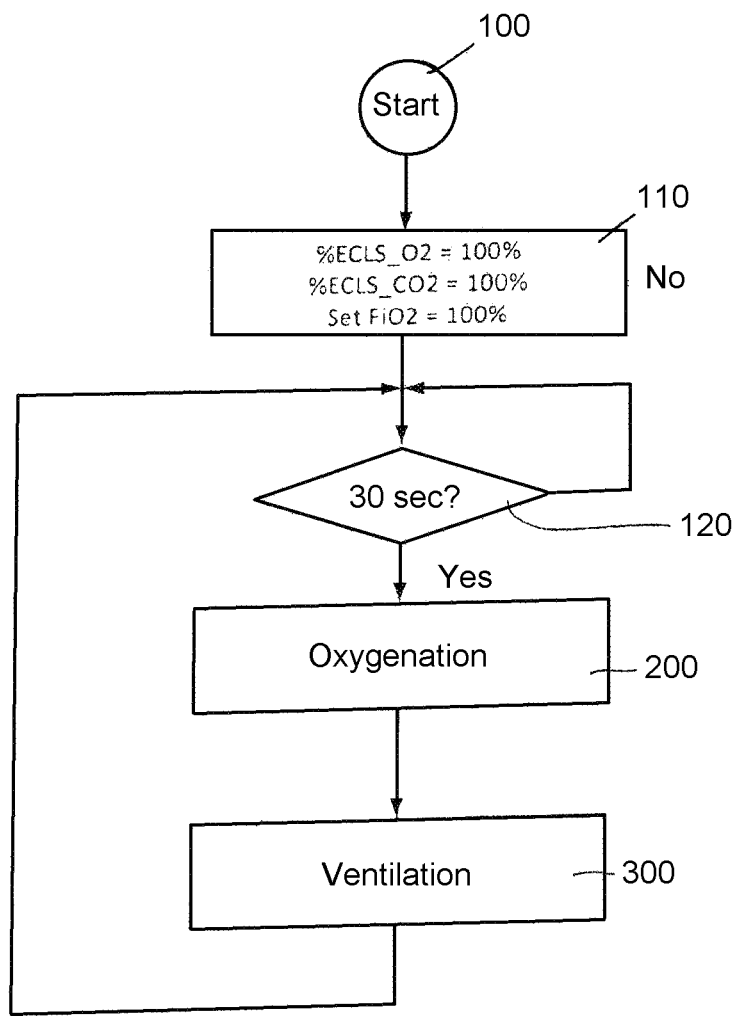
FIG. 3 shows a flow diagram illustrating an example of the procedure of coordinated cooperation between the device for mechanical ventilation and the ECLS device.

FIG. 3 illustrates, in the form of a flow diagram, the basic process of the coordinated cooperation between ventilation device 20 and ECLS device 50 in an example. The flow diagram according to FIG. 3, like the flow diagrams according to FIG. 4 and FIG. 5 to be described hereinafter, are restricted to a representation of the steps and parameters relevant with respect to the coordinated cooperation of ventilation device 20 and ECLS device 50, without any claim to comprehensiveness of the total course of the procedures illustrated.

After start of the process at 100, there are firstly set starting values for some parameters which are of relevance as regards the coordinated cooperation of ventilation device 20 and ECLS device 50 as indicated at 110. These are, above all, the parameters of the degree of extracorporeal support in oxygenation % ECLS_O2 and the degree of extracorporeal support in ventilation % ECLS_CO2. In accordance with the embodiment illustrated, both quantities are expressed as relative quantities which each are to show the proportion of the extracorporeal support in blood gas exchange (i.e., in oxygenation and ventilation, respectively) afforded by the ECLS device 50 in relation to the total support in blood gas exchange. In doing so, oxygenation and ventilation will be considered separately and expressed each by a separate degree of extracorporeal support % ECLS_O2 and % ECLS_CO2, respectively. A starting value is assigned both to the parameter % ECLS_O2 and to the parameter % ECLS_CO2. This starting value can be set manually. In selecting the starting values, the condition of the patient in general will be used as orientation, and one will follow an assessment as to the extent or proportion of the necessary additional extracorporeal blood gas exchange in order to arrive at a reasonable overall condition of the patient in cooperation with positive-pressure ventilation. As regards this assessment, it is recommended to proceed "conservatively," i.e., to definitely not underestimate the degree of extracorporeal support in oxygenation and ventilation, respectively, but rather in case of doubt, to select the starting values for % ECLS_O2 and % ECLS_CO2 rather too high. In the example illustrated, starting values of 100% each are selected for % ECLS_O2 and % ECLS_CO2, which means that the support in blood gas exchange at the beginning is afforded completely by extracorporeal blood gas exchange, so that the positive-pressure ventilation thus has no contributory effect at all.

In addition thereto, there is also set a starting value for the content of oxygen in the breathing gas FiO2 supplied to the airway by the ventilation device 20. In the embodiment illustrated in FIG. 3, a starting value of FiO2=100% is set, which means that the ventilation device supplies pure oxygen to the patient as soon as it contributes in supporting the blood gas exchange in addition to the ECLS device 50. The value set for FiO2 in this step, however, will change very rapidly as the ventilation device 20 is configured such that it will always select a best possible ventilation mode and, for the ventilation mode selected, will set the ventilation parameters such that a best possible ventilation state is obtained. In doing so, the ventilation device 20 as a rule will change the value of FiO2, in particular to a value clearly smaller than 100%.

Upon setting of the starting values, the procedure waits until a predetermined period of time has lapsed (step 120). This predetermined time determines the repetition rate of the renewed adjustment of the parameters for the ECLS device 50. It should be selected clearly longer than the time constant of the ventilation device 20, i.e., the time required for the ventilation device 20 on the average for adjusting to a new state. In the instant example, this time is 30 s.

After lapse of the predetermined time, the process enters into a procedure for setting relevant parameters with respect to oxygenation (step 200) followed by a procedure for setting relevant parameters with respect to ventilation (step 300).

This sequence then is repeated recurrently, i.e., the process waits again for the lapse of the predetermined time (step 120), whereupon oxygenation (step 200) takes place, followed by ventilation (step 300), etc.

Figure 4:
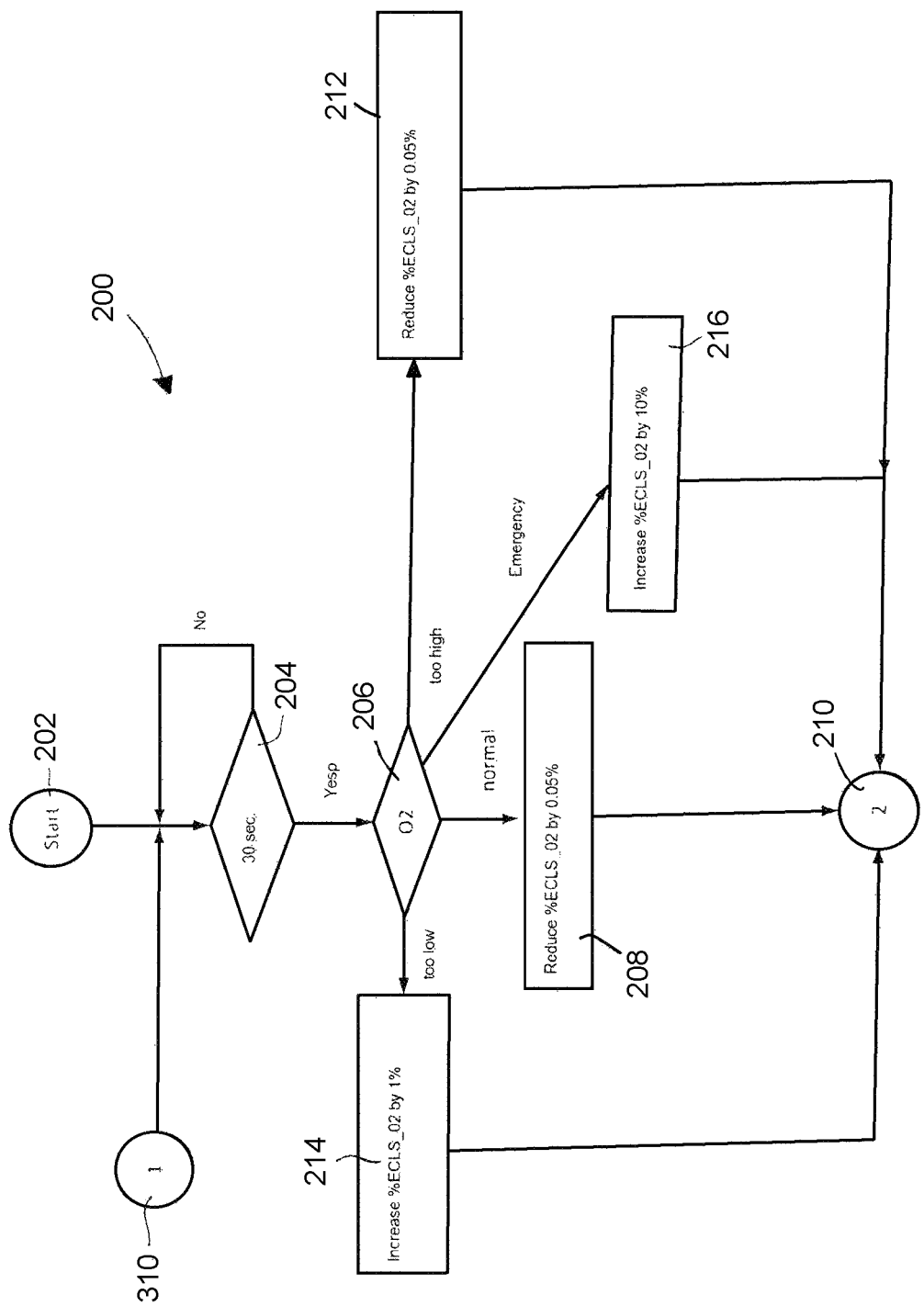
FIG. 4 shows a flow diagram illustrating further details of the procedures taking place in the oxygenation module according to FIG. 3.
Figure 6:
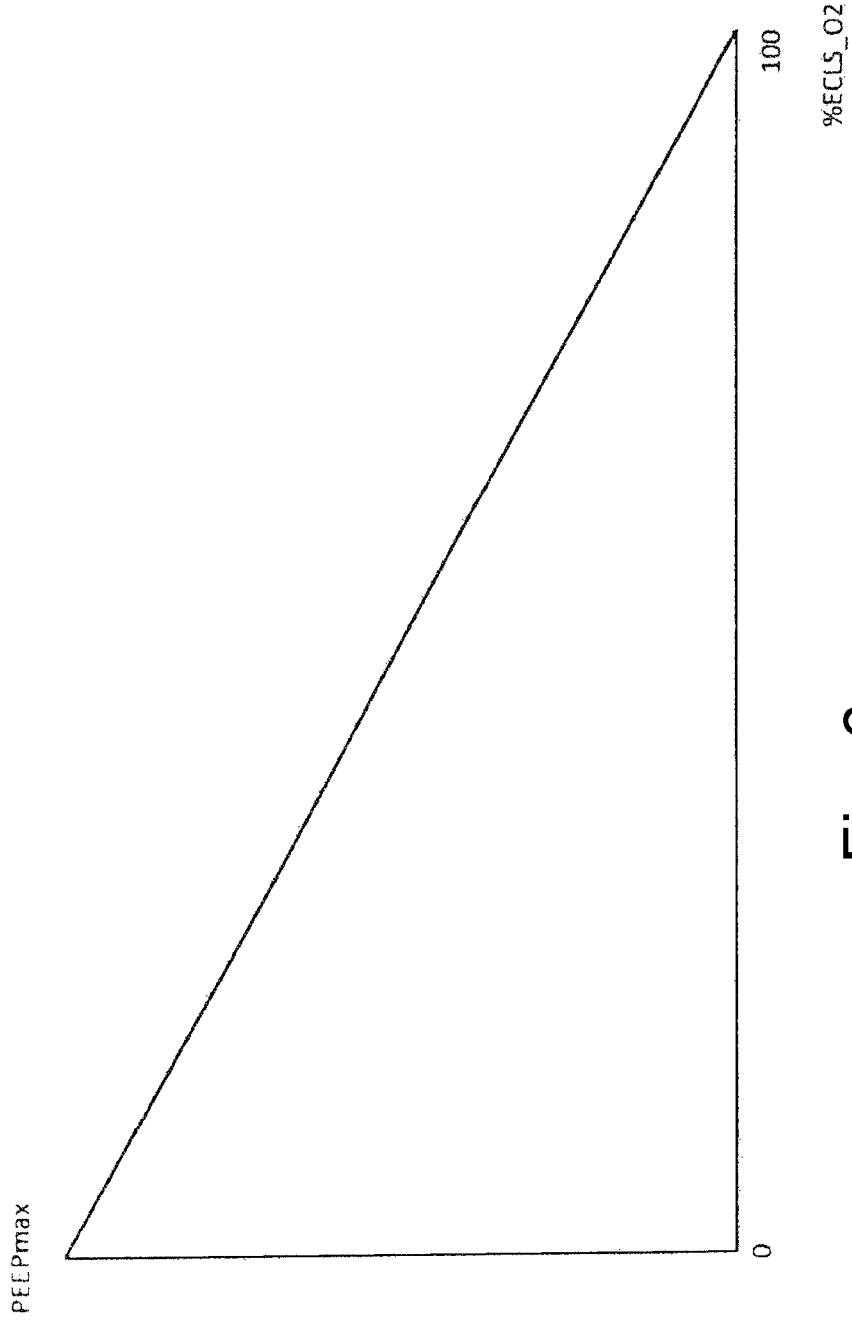
FIG. 6 shows a diagram qualitatively illustrating the correlation between the degree of extracorporeal support in oxygenation % ECLS_O2 and the maximum positive end-expiratory pressure PEEPmax.
Figure 7:
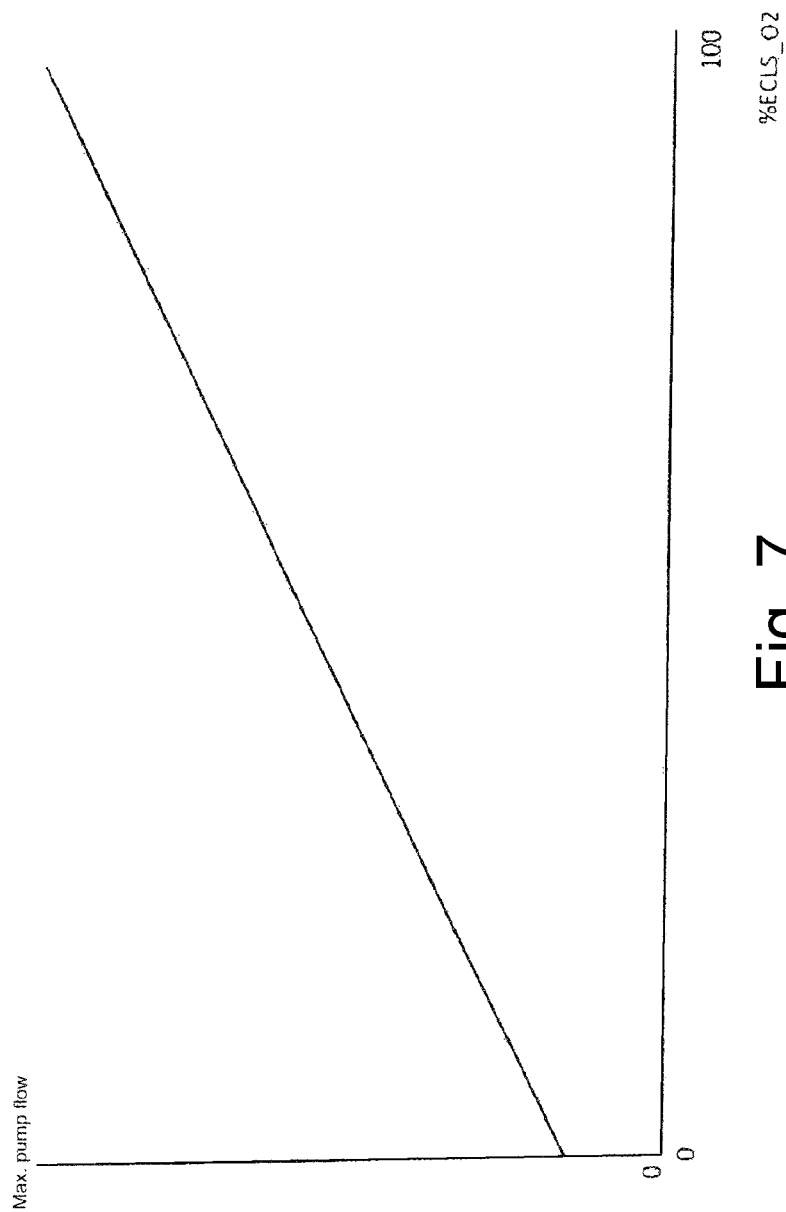
FIG. 7 shows a diagram qualitatively illustrating the correlation between the degree of extracorporeal support in oxygenation % ECLS_O2 and the maximum pump flow settable in the ECLS device.

FIG. 4 shows a flow diagram illustrating the procedures occurring in the oxygenation module 200 according to FIG. 3 in some more detail. After the start in step 202, the process first waits for a predetermined period of time (step 204) which in the example illustrated is 30 s. After lapse of this time, it is examined in step 206 whether the oxygenation of the blood circulation is sufficient. This can be effected by one or more of the aforementioned sensors, e.g., by determination of the oxygen saturation value SpO2 by pulse oximetry, or by an ongoing analysis of the blood gas values along with a determination of the oxygen concentration in the blood PaO2. If desired, the oxygen saturation SpO2 determined by pulse oximetry may be supplemented with values for PaO2 or SaO2 that are ascertained only sporadically by means of blood gas analysis. If the determination in step 206 has the result that the oxygen concentration or oxygen saturation is within a desired range, the parameter % ECLS_O2, expressing the degree of extracorporeal support in oxygenation, is reduced in step 210 by a predetermined first amount, which in the example illustrated is 0.05%. Starting with this moment of time, the relative proportions of the support in the blood gas exchange between extracorporeal blood gas exchange support by the ECLS device 50 and the support by positive-pressure ventilation change. This can be seen from the graphs in FIG. 6 and FIG. 7: the diagram shown in FIG. 6, which qualitatively illustrates the correlation between the degree of extracorporeal support in oxygenation % ECLS_O2 and the maximum positive end-expiratory pressure PEEPmax, reveals that the reduction of the parameter % ECLS_O2 by the first predetermined amount on the one hand increases the maximum positive end-expiratory pressure PEEPmax set for the ventilation device 20. On the other hand, the diagram according to FIG. 7, which qualitatively illustrates the correlation between the degree of extracorporeal support in oxygenation % ECLS_O2 and the maximum pump flow settable in the ECLS device, reveals that the maximum pump flow becomes lower when the parameter % ECLS_O2 is decreased by the first predetermined amount. However, the maximum pump flow corresponds to the maximum flow of blood that can flow in the extracorporeal ECLS circuit and accordingly is enriched with oxygen. This means that the basic conditions for extracorporeal support by the ECLS device 50 are set narrower whereas the basic conditions for support by the ventilation device 20 are set more leniently.

Figure 5:
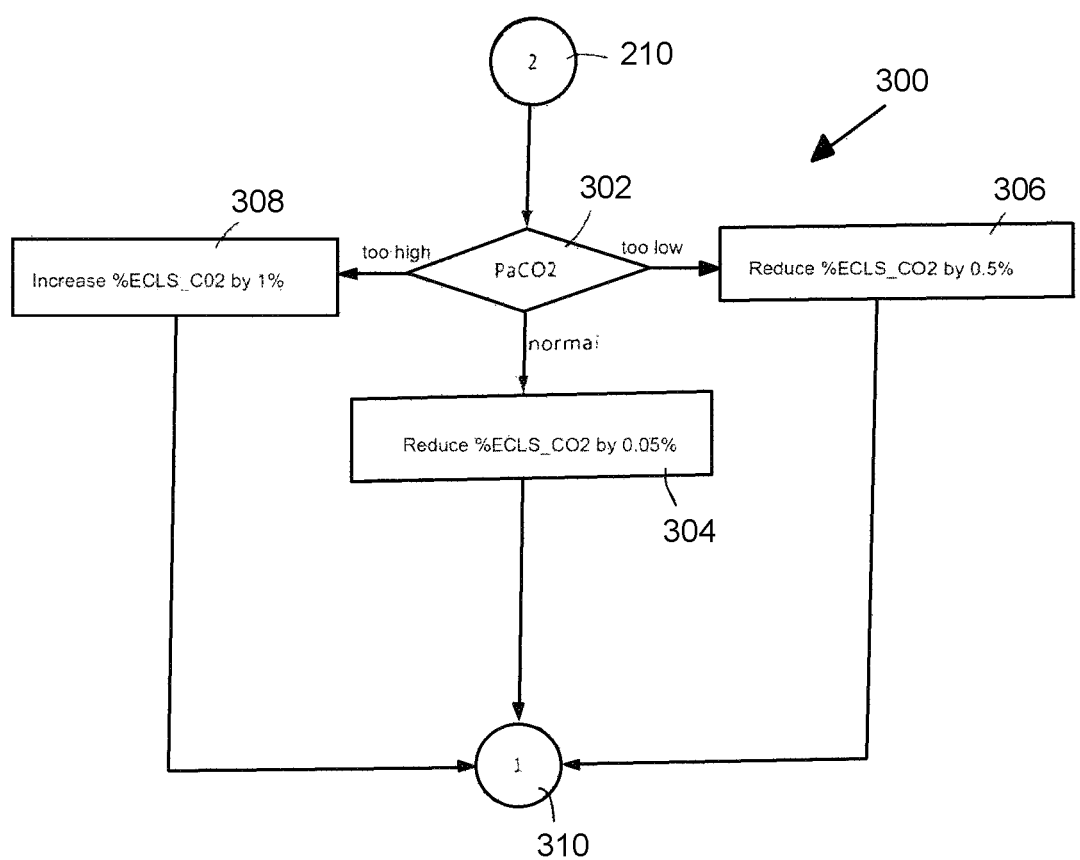
FIG. 5 shows a flow diagram illustrating further details of the procedures taking place in the ventilation module according to FIG. 3.

After step 208, the process arrives at point 2 in FIG. 4, bearing reference numeral 210. At this point, the procedure proceeds to the ventilation module 300 in FIG. 1. FIG. 5 shows a flow diagram illustrating further details of the procedures taking place in ventilation module 300.

Figure 8:
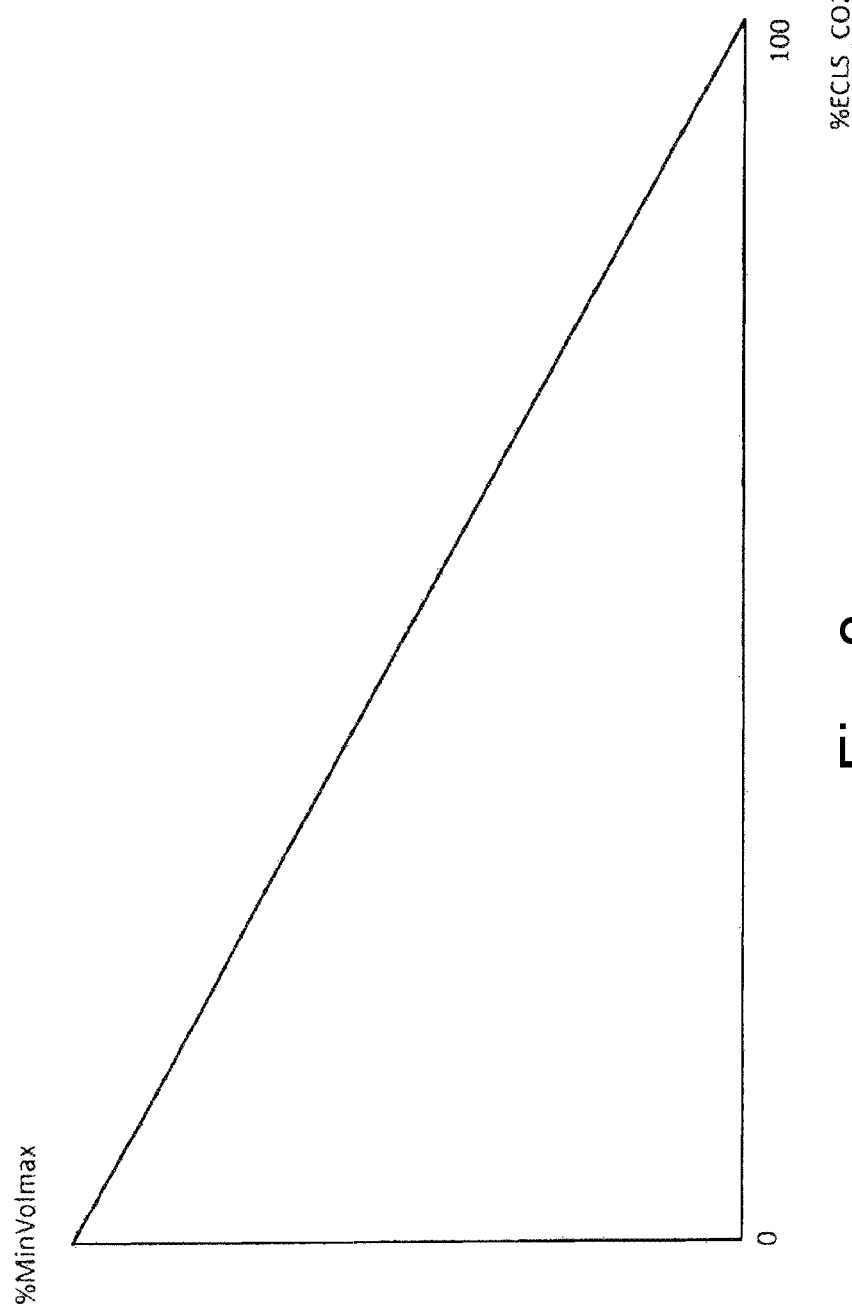
FIG. 8 shows a diagram qualitatively illustrating the correlation between the degree of extracorporeal support in ventilation % ECLS_CO2 and the maximum minute volume in positive-pressure ventilation.
Figure 9:
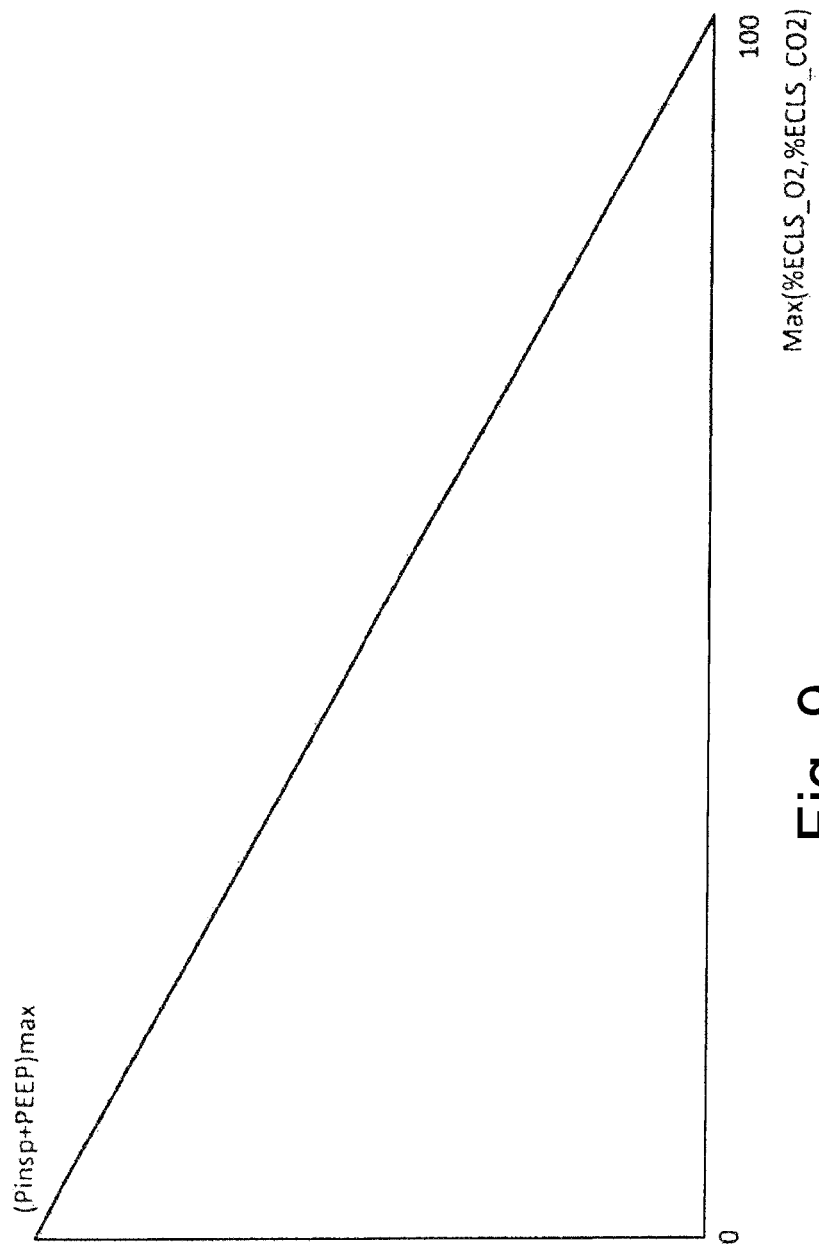
FIG. 9 shows a diagram qualitatively illustrating the correlation between the maximum of the degree of extracorporeal support in oxygenation % ECLS_C2 and the degree of extracorporeal support in ventilation % ECLS_CO2, on the one hand, as well as the maximum airway pressure (Pinsp+PEEP)max in positive-pressure ventilation.
Figure 10:
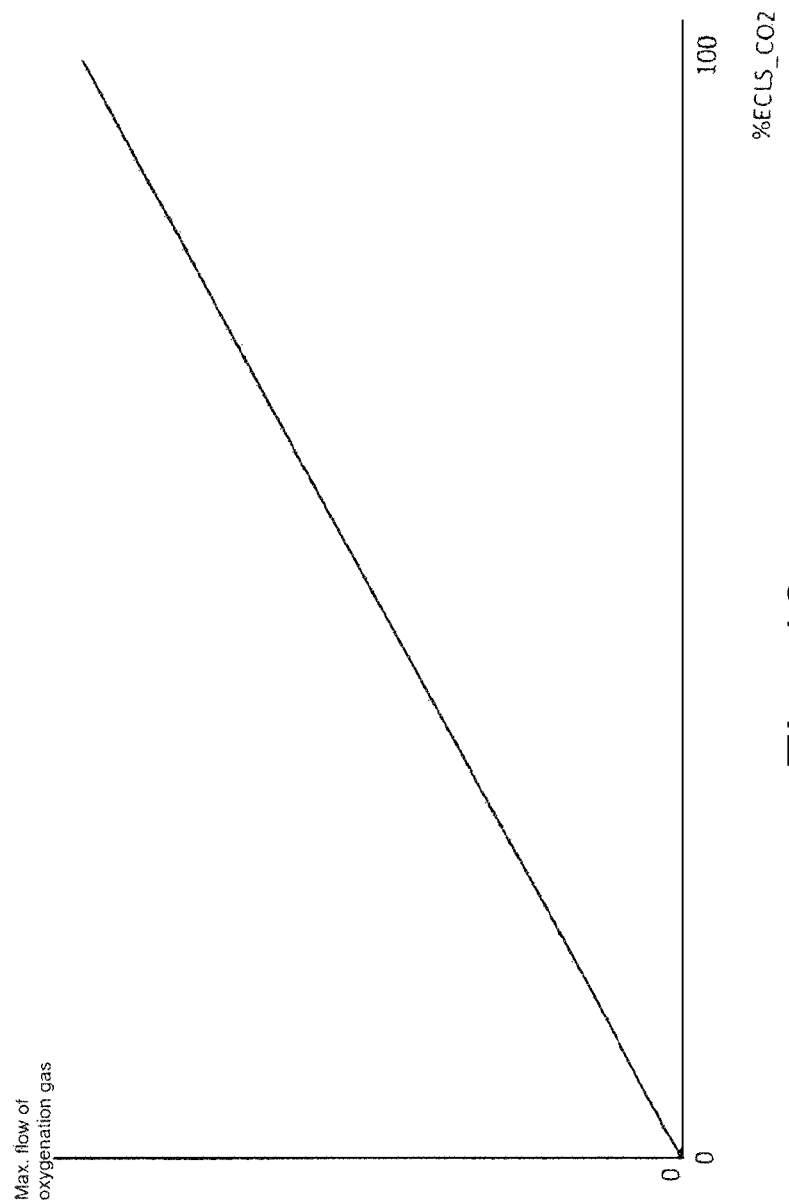
FIG. 10 shows a diagram qualitatively illustrating the correlation between the degree of extracorporeal support in ventilation % ECLS_CO2 and the maximum flow of oxygenation gas settable in the ECLS device.

Firstly, the process again waits for the lapse of a predetermined period of time (step 302), which in the example illustrated is 30 s. After lapse of this time, it is examined in step 304 whether the ventilation of the blood circulation is sufficient. This can be effected by means of one or more of the aforementioned sensors, for example by an ongoing analysis of the blood gas values along with a determination of the carbon dioxide concentration in the blood PaCO2 and the corresponding carbon dioxide saturation SaCO2, respectively. A measurement of the CO2 content in the exhaled air, indicated in FIGS. 1 and 2 as PetCO2, may be used as well. If desired, such a measurement may be supplemented by values for PaCO2 or SaCO2 ascertained only sporadically by means of blood gas analysis. When the determination in step 302 has the result that the carbon dioxide concentration or carbon dioxide saturation is within a desired range, the parameter % ECLS_CO2, which expresses the degree of extracorporeal support in ventilation, is reduced in step 304 by a predetermined second amount, in the example illustrated by 0.05%. Starting with this moment of time, the relative proportions of the support in the blood gas exchange between extracorporeal blood gas exchange support by the ECLS device 50 and the support by positive-pressure ventilation change. This can be seen from the graphs in FIGS. 8 to 10: the diagram shown in FIG. 8, which qualitatively illustrates the correlation between the degree of extracorporeal support in ventilation % ECLS_CO2 and the maximum minute volume in positive-pressure ventilation % MinVolMax, reveals that the reduction of the parameter % ECLS_CO2 by the second predetermined amount on the one hand increases the maximum minute volume % MinVolMax set for the ventilation device 20. On the other hand, the diagram according to FIG. 9, which qualitatively illustrates the correlation between the degree of extracorporeal support in oxygenation % ECLS_O2 and the degree of extracorporeal support in ventilation % ECLS_CO2 on the one hand, and the maximum airway pressure (Pinsp+PEEP)max in positive-pressure ventilation, reveals that also the maximum airway pressure (Pins+PEEP)max becomes higher in positive-pressure ventilation when both parameters have decreased, % ECLS_O2 by the first predetermined amount and % ECLS_CO2 by the second predetermined amount. Both an increase in the maximum minute volume and an increase in the maximum permitted airway pressure allow an in total greater influence of positive-pressure ventilation in the support of the blood gas exchange exerted by the ventilation system in total. In addition, FIG. 10 reveals that the reduction of the parameter % ECLS_CO2 by the second predetermined amount still has an additional effect. It can be seen from the diagram shown in FIG. 10 that qualitatively the maximum flow of oxygenation gas settable in the ECLS device becomes lower with a decreasing degree of extracorporeal support in ventilation % ECLS_CO2. Thus, a reduction of the parameter % ECLS_CO2 also entails a reduction in the blood gas exchange obtainable in total by means of ECLS as the basic conditions for the extracorporeal support by the ECLS device are set narrower. In contrast thereto, the basic conditions for support by positive-pressure ventilation are set more leniently.

In total, this has the effect that at point 310 the influence of positive-pressure ventilation has increased in total at the expense of the influence of extracorporeal blood gas exchange. And this although the target values set with respect to the enrichment of blood with oxygen and the depletion of blood from CO2, respectively, could be fulfilled with the setting selected initially for the procedure.

Upon arrival at point 1 in FIG. 5, which bears reference numeral 310, the process returns to point 1 in FIG. 4 which also bears reference numeral 310. This means, there follows a new waiting period, followed by a new detection of the state as regards oxygenation and possibly a new setting of the parameter % ECLS_O2.

The procedure described means in its entirety that the ventilation system 10 has a tendency to develop from a selected initial state in a direction in which positive-pressure ventilation is gaining increasing influence and the extracorporeal blood gas exchange increasingly loses influence, at least as long as target values concerning oxygenation and ventilation and set by the combined effect of positive-pressure ventilation and extracorporeal blood gas exchange can be achieved. Thus, the ventilation system 10 of itself, without requiring interventions from outside, adjusts to a state in which positive-pressure ventilation takes as much influence as possible and the extracorporeal blood gas exchange is supportive just to a degree that is necessary. This development is promoted by the ECLS device 50, but not by the ventilation device 20. In the end, this leads to a gradual, but continuous development with little or no impacts on the ECLS device by the ventilation device 20 adapting to respective basic conditions set by the ECLS device 50.

Should the case occur that the concentration of oxygen in the blood detected in step 206 does not correspond to the desired target value, but rather is too low or too high, it is provided that the parameter % ECLS_O2 indicating the degree of extracorporeal support in oxygenation is reduced by a third amount which is greater than the first amount (step 212), or is increased by a fourth amount (step 214). The third amount is greater than the first amount, so that the proportion of positive-pressure ventilation thereafter increases even faster than in case of merely reaching the desired target value for the oxygen concentration in the blood. To the contrary, the increase of % ECLS_O2 by the fourth amount has the effect that the support by positive-pressure ventilation thereafter does no longer increase, but to the contrary decreases. This takes account of the fact that in such a situation the patient's condition does not permit a further increase of the percentage of positive-pressure ventilation. Should the desired oxygen concentration be drastically missed, an emergency is concluded, with the consequence that the parameter % ECLS_O2 is drastically increased, in the example by 10% (step 216) so that a sufficient blood gas exchange can be ensured in the extracorporeal circuit.

Similar mechanisms are also applicable for the ventilation module 300. Should the situation arise that the concentration of carbon dioxide in the blood, as detected in step 302, does not correspond to the desired target value, but rather is too high or too low, it is provided that the parameter % ECLS_CO2 indicating the degree of extracorporeal support in ventilation is reduced by a fifth amount which is greater than the second amount (step 306), or is increased by a sixth amount (step 308). The fifth amount is greater than the second amount, so that the proportion of positive-pressure ventilation thereafter increases even faster than in the case of merely reaching the desired target value for the carbon dioxide concentration in the blood. To the contrary, the increase of % ECLS_CO2 by the sixth amount has the effect that the support by positive-pressure ventilation thereafter does no longer increase, but to the contrary decreases. This takes account of the fact that, in such a situation, the patient's condition does not permit a further increase of the proportion of positive-pressure ventilation.

Figure 11:
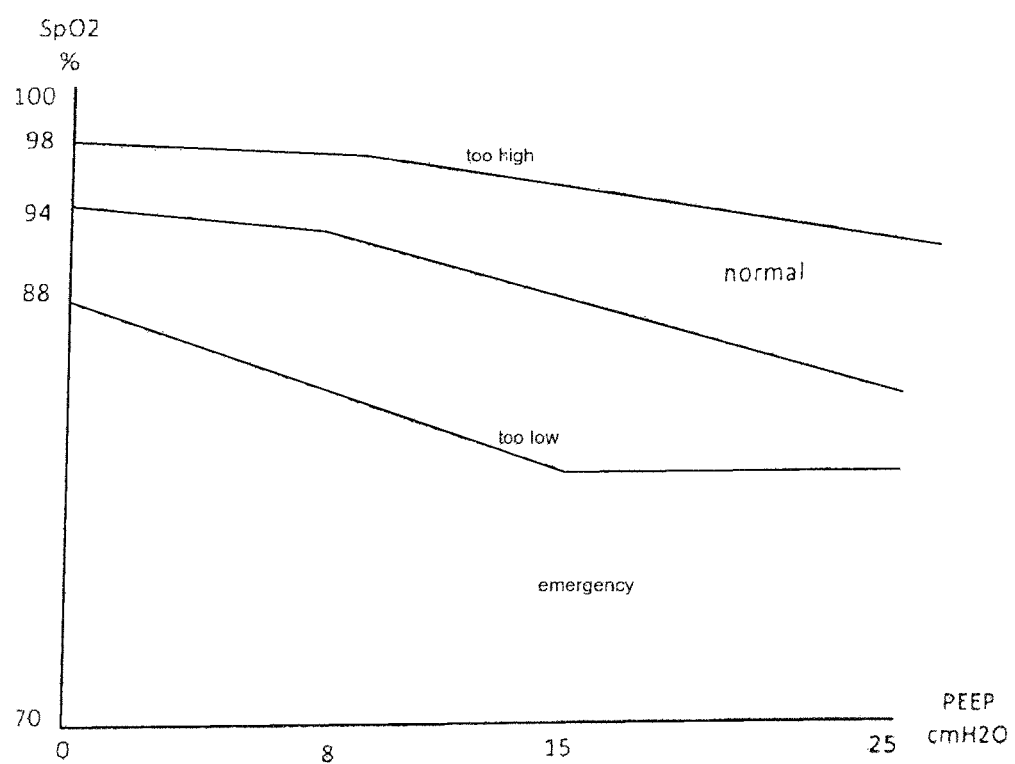
FIG. 11 shows a diagram qualitatively illustrating which values for the oxygen saturation value SpO2 measured by means of pulse oximetry, at the respective prevailing positive end-expiratory pressure PEEP, are deemed too high, too low, normal or even as an emergency, and in the query according to FIG. 4 result in corresponding changes of the parameter % ECLS_O2.

FIG. 11 shows a diagram that qualitatively illustrates which values for the oxygen saturation value SpO2 measured by pulse oximetry, with respect to the respective prevailing positive end-expiratory pressure PEEP, are deemed too high, too low, normal or even as an emergency, and in the query according to FIG. 4 leads to corresponding changes of the parameter % ECLS_O2.

Figure 12:
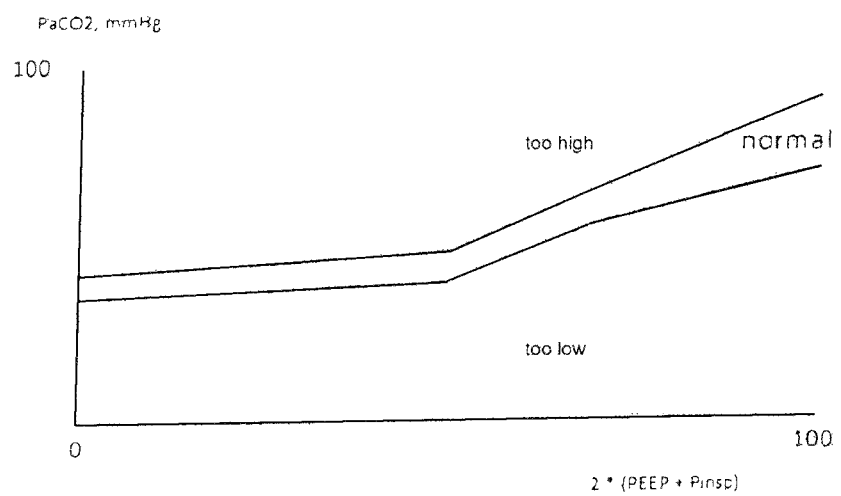
FIG. 12 shows a diagram qualitatively illustrating which values for the carbon dioxide concentration PaCO2 measured in the arterial blood, at the respective prevailing maximum airway pressure (Pinsp+PEEP), are deemed too high, too low or normal, and in the query according to FIG. 5 result in corresponding changes of the parameter % ECLS_CO2.

FIG. 12 shows a diagram that qualitatively illustrates which values for the concentration of CO2 PaCO2 determined in arterial blood, with regard to the respective prevailing maximum airway pressure (Pinsp+PEEP), are deemed too high, too low or normal, and in the query according to FIG. 5 lead to corresponding changes of the parameter % ECLS_CO2.

In all of the diagrams illustrated, in particular in the correlations illustrated in FIGS. 6 to 12, it is to be noted that merely a qualitative course is to be illustrated. There is no intention to make quantitative statements by this. In addition, the linear course of the relationships merely represents a simplification. The true course may deviate in partial sections or even completely from the linear course. What is of importance is the respective outlined increasing or decreasing tendency of the respective parameters with an increasing value of % ECLS_O2 and % ECLS_CO2, respectively.

The invention claimed is:

1. A ventilation system for supporting blood gas exchange by mechanical ventilation and extracorporeal blood gas exchange, the ventilation system comprising:
    a ventilation device for mechanical ventilation of lungs of a patient,
    an extracorporeal lung support (ECLS) device for extracorporeal blood gas exchange, and
    a controller coupled to the ventilation device,
    wherein the ventilation system is designed to perform both mechanical respiratory support by the ventilation device and extracorporeal blood gas exchange by the ECLS device in a coordinated automated manner that is configured to support the gas exchange in blood of the patient,
    wherein the ECLS device is configured to adjust and set a level of the extracorporeal blood gas exchange, and wherein the controller coupled to the ventilation device is configured to receive the level of the extracorporeal blood gas exchange set by the ECLS device and determine a maximum positive end-expiratory pressure based on the level of the extracorporeal blood gas exchange received from the ECLS device such that the maximum positive end-expiratory pressure fluctuates in real time in response to the level of the extracorporeal blood gas exchange received from the ECLS device,
    wherein the ventilation device is configured to be adjusted in an automated manner by the controller coupled to the ventilation device to a level of mechanical respiratory support, wherein the controller coupled to the ventilation device is configured to autonomously monitor ventilation parameters, including a positive end-expiratory pressure, of the ventilation device and adjust the positive end-expiratory pressure in a closed-loop control system such that the positive end-expiratory pressure does not exceed the maximum positive end-expiratory pressure, and wherein the level of extracorporeal blood gas exchange set by the ECLS device is associated with a degree of extracorporeal support in oxygenation that includes enriching the blood with oxygen.

2. The ventilation system of claim 1, wherein the level of the extracorporeal blood gas exchange is preselected by the ECLS device in an automated or manual manner.

3. The ventilation system of claim 2, wherein the ECLS device sets a target value for the level of the extracorporeal blood gas exchange.

4. The ventilation system of claim 1, wherein the ventilation device, for a respective affected setting of the level of the extracorporeal blood gas exchange by the ECLS device, automatically controls the mechanical respiratory support by positive-pressure ventilation.

5. The ventilation system of claim 4, wherein the ventilation device is designed to select, in an automated manner and in a range of set ventilation parameters, a ventilation state to be set by the ventilation device, and to control the ventilation device such that the ventilation device assumes the selected ventilation state.

6. The ventilation system of claim 5, wherein the set ventilation parameters are derived from the level of the extracorporeal blood gas exchange set by the ECLS device.

7. The ventilation system of claim 1, wherein the maximum positive end-expiratory pressure increases with a decreasing degree of extracorporeal support in oxygenation.

8. The ventilation system of claim 1, wherein the degree of extracorporeal support in oxygenation is configured to determine a maximum value for blood flow taken from the patient by the ECLS device.

9. The ventilation system of claim 8, wherein the maximum value for the blood flow taken from the patient by the ECLS device increases with an increasing degree of extracorporeal support in oxygenation.

10. The ventilation system of claim 1, wherein the level of the extracorporeal blood gas exchange set by the ECLS device is associated with a degree of extracorporeal support in ventilation that includes removing carbon dioxide ($CO_2$) from the blood.

11. The ventilation system of claim 10, wherein the degree of extracorporeal support in ventilation determines a maximum minute volume for mechanical ventilation.

12. The ventilation system of claim 11, wherein the maximum minute volume increases with a decreasing degree of extracorporeal support in ventilation.

13. The ventilation system of claim 10, wherein the degree of extracorporeal support in ventilation determines a maximum airway pressure for mechanical ventilation.

14. The ventilation system of claim 13, wherein the maximum airway pressure increases with a decreasing degree of the maximum value of extracorporeal support in oxygenation and extracorporeal support in ventilation.

15. The ventilation system of claim 10, wherein the degree of extracorporeal support in ventilation is configured to determine a maximum value of the flow of oxygenation gas that the ECLS device supplies to blood taken from the patient's blood circulation.

16. The ventilation system of claim 15, wherein the maximum value of the flow of oxygenation gas that the ECLS device supplies to blood taken from the patient's blood circulation, increases with an increasing degree of the extracorporeal support in ventilation.

17. The ventilation system of claim 1, wherein at a respective level of the extracorporeal blood gas exchange, the ECLS device examines, after expiration of a predetermined period of time, whether, at the level of the extracorporeal blood gas exchange, a predetermined target state for the blood gas exchange is reached by the ventilation device and the ECLS device together.

18. The ventilation system of claim 17, wherein the predetermined target state for the blood gas exchange is a parameter that defines a concentration of oxygen ($O_2$) in the blood.

19. The ventilation system of claim 17, wherein the predetermined target state for the blood gas exchange is a parameter that defines a concentration of $CO_2$ in the blood.

20. The ventilation system of claim 17, wherein the ECLS device, upon reaching the predetermined target state, reduces the level of the extracorporeal blood gas exchange.

21. The ventilation system of claim 17, wherein the ECLS device, upon reaching the predetermined target state which is a set value of a concentration of $O_2$ in the blood, reduces the level of the extracorporeal blood gas exchange in oxygenation by a first predetermined amount.

22. The ventilation system of claim 17, wherein the ECLS device, upon reaching the predetermined target state which is a set value of a concentration of $O_2$ in the blood, reduces the degree of the extracorporeal support in ventilation by a second predetermined amount.

23. The ventilation system of claim 17, wherein the ECLS device examines in recurrent intervals of time whether, at the respective level of the extracorporeal blood gas exchange, a predetermined target value for the blood gas exchange is reached by the ventilation device and the ECLS device together.

24. The ventilation system of claim 23, wherein a time interval for the examination by the ECLS device is greater than a time constant of the ventilation device.

25. The ventilation system of claim 1, wherein the ECLS device starts from a preset starting value for the level of the extracorporeal blood gas exchange.

26. The ventilation system of claim 25, wherein the starting value corresponds to a maximum level for the level of the extracorporeal blood gas exchange.

27. The ventilation system of claim 25, wherein the starting value is a reference value for a reduction and increase, respectively, of the level of the extracorporeal blood gas exchange.

28. A method comprising:
coordinating cooperation of a ventilation device for mechanical positive-pressure ventilation of lungs of a patient and an ECLS device for extracorporeal blood gas exchange of blood of the patient, wherein both mechanical respiratory support by the ventilation device and an extracorporeal blood gas exchange by the ECLS device, are performed in a coordinated automated manner in order to support gas exchange in the blood of the patient, wherein the ventilation device is coupled to a controller, wherein the ECLS device adjusts and sets a level of the extracorporeal blood gas exchange, and wherein the controller coupled to the ventilation device is configured to receive the level of the extracorporeal blood gas exchange set by the ECLS device and determine a maximum positive end-expiratory pressure based on the level of the extracorporeal blood gas exchange received from the ECLS device such that the maximum positive end-expiratory pressure fluctuates in real time in response to the level of the extracorporeal blood gas exchange received from the ECLS device, wherein the ventilation device adjusts in an automated manner by the controller to a level of the mechanical respiratory support, wherein the controller is configured to autonomously monitor ventilation parameters, including a positive end-expiratory pressure, and adjust the positive end-expiratory pressure, in a closed-loop control system, wherein the level of extracorporeal blood gas exchange set by the ECLS device is associated with a degree of extracorporeal support in oxygenation that includes enriching the blood with oxygen, and wherein the degree of extracorporeal support in oxygenation determines a maximum positive end-expiratory pressure for the closed-loop control of the positive end-expiratory pressure in the mechanical ventilation such that the positive end-expiratory pressure does not exceed the maximum positive end-expiratory pressure.

* * * * *